(12) United States Patent
Blanchard et al.

(10) Patent No.: US 9,625,466 B2
(45) Date of Patent: Apr. 18, 2017

(54) SIGNAL AMPLIFICATION METHODS FOR THE IMAGING OF PROTEIN SYNTHESIS AND NEUROTRANSMITTER TRANSPORT

(75) Inventors: Scott C. Blanchard, New York, NY (US); Roger B. Altman, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 111 days.

(21) Appl. No.: 14/110,372

(22) PCT Filed: Apr. 6, 2012

(86) PCT No.: PCT/US2012/032601
§ 371 (c)(1),
(2), (4) Date: Jan. 10, 2014

(87) PCT Pub. No.: WO2012/139046
PCT Pub. Date: Oct. 11, 2012

(65) Prior Publication Data
US 2014/0127681 A1    May 8, 2014

Related U.S. Application Data

(60) Provisional application No. 61/472,489, filed on Apr. 6, 2011.

(51) Int. Cl.
*G01N 33/68* (2006.01)
*C07K 14/47* (2006.01)

(52) U.S. Cl.
CPC ............. *G01N 33/68* (2013.01); *C07K 14/47* (2013.01)

(58) Field of Classification Search
CPC .................................................. G01N 33/542
See application file for complete search history.

(56) References Cited

U.S. PATENT DOCUMENTS

| | | |
|---|---|---|
| 2002/0058273 A1 | 5/2002 | Shipwash |
| 2004/0109887 A1 | 6/2004 | Wyatt et al. |
| 2005/0282173 A1 | 12/2005 | Mandecki |
| 2010/0151518 A1 | 6/2010 | Bergquist et al. |

FOREIGN PATENT DOCUMENTS

| | | |
|---|---|---|
| EP | 2033655 A1 | 3/2009 |
| WO | 2010/096720 A2 | 8/2010 |

OTHER PUBLICATIONS

Wlodek Mandecki et al (Fluorescence enhancement on silver nanostructures: studies of components of ribosomal translation in vitro Single Molecule Spectroscopy and Imaging edited by Jörg Enderlein, Zygmunt K. Gryczynski, Rainer Erdmann Proc. of SPIE vol. 6862, 68620T, (2008).*
Perla-Kajan (Properties of *Escherichia coli* EF-TU mutants designed for fluorescence resonance energy transfer from tRNA molecules Protein Eng Des Sel. Mar. 2010; 23(3): 129-136.*
Jaskolski et al. Synaptic Receptor Trafficking: The Lateral Point of View. Neuroscience 158 (2009) 19-24.*
Abrahamson, J.K. et al., "Direct determination of the association constant between elongation factor Tu•GTP and aminoacyl-tRNA using fluorescence" Biochemistry (1985) pp. 692-700, vol. 24.
Aitken, C.E. et al., "An oxygen scavenging system for improvement of dye stability in single-molecule fluorescence experiments" Biophys. J. (Mar. 2008) pp. 1826-1835, vol. 94.
Blanchard, S. C. et al., "tRNA selection and kinetic proofreading in translation" Nature Structural & Molecular Biology (Oct. 2004) pp. 1008-1014, vol. 11, No. 10.
Blanchard, S. C. et al., "tRNA dynamics on the ribosome during translation" Proc Natl Acad Sci USA (Aug. 31, 2004) pp. 12893-12898, vol. 101, No. 35.
Dave, R. et al., "Mitigating Unwanted Photophysical Processes for Improved Single-Molecule Fluorescence Imaging" Biophys J (Mar. 2009) pp. 2371-2381, vol. 96.
Dorner, S. et al., "The hybrid state of tRNA binding is an authentic translation elongation intermediate" Nature Structural & Molecular Biology (Mar. 2006) pp. 234-241, vol. 13, No. 3.
Gromadski, K.B. et al., "A uniform response to mismatches in codon-anticodon complexes ensures ribosomal fidelity" Molecular Cell (Feb. 3, 2006) pp. 369-377, vol. 21.

(Continued)

*Primary Examiner* — Kagnew H Gebreyesus
(74) *Attorney, Agent, or Firm* — Scully Scott Murphy & Presser

(57) ABSTRACT

The present invention describes the synthesis of biological samples that can be used for the purpose of enhancing the signal-to-noise ratios achievable during the imaging of protein synthesis, amino acid transport and neurotransmitter transport, particularly in applications where single-molecule resolution is demanded. The present invention provides quencher-labeled elongation factor (EF-Tu) and fluorophore-labeled tRNA. When these molecules are present in a ternary complex with GTP, the fluorescently-labeled tRNA is quantitatively quenched. Once the tRNA is incorporated into an actively translating ribosome, however, a burst of fluorescence is released and can be detected by a variety of techniques, including smFRET imaging. The invention further provides novel EF-Tu constructs for achieving quencher labeling at high levels while retaining native or near native activity in the translation reactions, as well as methods for preparing stable ternary complexes, methods of protein sequencing, methods of detecting amino acid transport using a proteoliposome assay system and the proteoliposomes systems and methods of imaging translation events in single living cells. The present invention should have an immediate impact on next-generation sequencing technologies and the detection of neurotransmitter transporter activities in both in vitro and in vivo settings, a critical component of drug activity/screening assays targeting this important class of molecules.

14 Claims, 17 Drawing Sheets

(56) References Cited

OTHER PUBLICATIONS

Johansson, M. et al., "Rate and accuracy of bacterial protein synthesis revisited" Curr Opin Microbiol (2008) pp. 141-147, vol. 11.
Kim, H.D. et al., "Fluctuations of Transfer RNAs between Classical and Hybrid States" Biophys J (Nov. 2007) pp. 3575-3582, vol. 93.
Lee, T.-H. et al., "The role of fluctuations in tRNA selection by the ribosome" PNAS (Aug. 21, 2007) pp. 13661-13665, vol. 104, No. 34.
Louie, A. et al., "Kinetic Studies of *Escherichia coli* Elongation Factor Tu-Guanosine 5'-Triphosphate-Aminoacyl-tRNA Complexes" Biochemistry (1985) pp. 6433-6439, vol. 24.
Lovmar, M. et al., "Rate, accuracy and cost of ribosomes in bacterial cells" Biochimie (2006) pp. 951-961, vol. 88.
Munro, J.B. et al., "Spontaneous formation of the unlocked state of the ribosome is a multistep process" PNAS (Jan. 12, 2010) pp. 709-714, vol. 107, No. 2.
Munro, J.B. et al., "Identification of two distinct hybrid state intermediates on the ribosome" Mol Cell (Feb. 23, 2007) pp. 505-517, vol. 25.
Munro, J.B. et al., "Navigating the ribosome's metastable energy landscape" Trends Biochem Sci (2009) pp. 390-400, vol. 34, No. 8.
Ninio, J., "Multiple stages in codon-anticodon recognition: double-trigger mechanisms and geometric constraints" Biochimie (2006) pp. 963-992, vol. 88.
Nirenberg, M. et al., "Rna Codewords and Protein Synthesis. The Effect of Trinucleotides Upon the Binding of Srna to Ribosomes" Science (Sep. 25, 1964) pp. 1399-1407, vol. 145.
Ogle, J.M. et al., "Insights into the decoding mechanism from recent ribosome structures" Trends Biochem Sci (May 2003) pp. 259-266, vol. 28, No. 5.
Pan, D. et al., "Kinetically competent intermediates in the translocation step of protein synthesis" Mol Cell (Feb. 23, 2007) pp. 519-529, vol. 25.
Parker, J., "Errors and alternatives in reading the universal genetic code" Microbiol Rev (Sep. 1989) pp. 273-298, vol. 53, No. 3.
Parmeggiani, A. et al., "Structural basis of the action of pulvomycin and GE2270 A on elongation factor Tu" Biochemistry (2006) pp. 6846-6857, vol. 45, No. 22.
Parmeggiani, A. et al., "Enacyloxin IIa pinpoints a binding pocket of elongation factor Tu for development of novel antibiotics" J Biol Chem (Feb. 3, 2006) pp. 2893-2900, vol. 281, No. 5.
Perla-Kajan, J. et al., "Properties of *Escherichia coli* EF-Tu mutants designed for fluorescence resonance energy transfer from tRNA molecules" Protein Eng. Des. Sel. (2010) pp. 129-136, vol. 23, No. 3.
Peske, F. et al., "Conformational changes of the small ribosomal subunit during elongation factor G-dependent tRNA-mRNA translocation" J Mol Biol (2004) pp. 1183-1194, vol. 343.
Petrov, A. et al., "Dynamics of the translational machinery" Curr Opin Struct Biol (2011) pp. 137-145, vol. 21.
Qin, F., "Restoration of single-channel currents using the segmental k-means method based on hidden Markov modeling" Biophys J (Mar. 2004) pp. 1488-1501, vol. 86.
Qin, F. et al., "Estimating single-channel kinetic parameters from idealized patch-clamp data containing missed events" Biophys J (Jan. 1996) pp. 264-280, vol. 70.
Ramakrishnan, V., "Ribosome structure and the mechanism of translation" Cell (Feb. 22, 2002) pp. 557-572, vol. 108.
Rodnina, M.V., "Long-range signalling in activation of the translational GTPase EF-Tu" Embo J (2009) pp. 619-620, vol. 28, No. 6.
Rodnina, M. V. et al., "Recognition and selection of tRNA in translation" FEBS Lett (2005) pp. 938-942, vol. 579.
Rush, J.S. et al., "New Aldehyde Tag Sequences Identified by Screening Formylglycine Generating Enzymes in Vitro and in Vivo" J. Am. Chem. Soc. (2008) pp. 12240-12241, vol. 130.
Schmeing, T. M. et al., "What recent ribosome structures have revealed about the mechanism of translation" Nature (Oct. 29, 2009) pp. 1234-1242, vol. 461.
Schmeing, T. M. et al., "The crystal structure of the ribosome bound to EF-Tu and aminoacyl-tRNA" Science (Oct. 30, 2009) pp. 668-694, vol. 326.
Schuette, J.C. et al., "GTPase activation of elongation factor EF-Tu by the ribosome during decoding" EMBO J. (2009) pp. 755-765, vol. 28.
Semenkov, Y.P. et al., "Energetic contribution of tRNA hybrid state formation to translocation catalysis on the ribosome" Nat Struct Biol (Nov. 2000) pp. 1027-1031, vol. 7, No. 11.
Sherlin, L.D. et al., "Hasty decisions on the ribosome" Nat Struct Mol Biol (Mar. 2004) pp. 206-208, vol. 11, No. 3.
Studer, S.M. et al., "Rapid kinetic analysis of EF-G-dependent mRNA translocation in the ribosome" J Mol Biol (2003) pp. 369-381, vol. 327.
Uemura, S. et al., "Real-time tRNA transit on single translating ribosomes at codon resolution" Nature (Apr. 15, 2010) pp. 1012-1017, vol. 464, No. 7291.
Villa, E. et al., "Ribosome-induced changes in elongation factor Tu conformation control GTP hydrolysis" PNAS (Jan. 27, 2009) pp. 1063-1068, vol. 106, No. 4.
Walker, S.E. et al., "Role of hybrid tRNA-binding states in ribosomal translocation" PNAS (Jul. 8, 2008) pp. 9192-9197, vol. 105, No. 27.
Wang, Y. et al., Single-molecule structural dynamics of EF-G-ribosome interaction during translocation Biochemistry (2007) pp. 10767-10775, vol. 46.
Yin, J. et al., "Site-specific protein labeling by Sfp phosphopantetheinyl transferase" Nat Protoc (2006) pp. 280-285, vol. 1, No. 1.
Young, T.S. et al., "Identification of the thiazolyl peptide GE37468 gene cluster from Streptomyces ATCC 55365 and heterologous expression in Streptomyces lividans" PNAS (Aug. 9, 2011) pp. 13053-13058, vol. 108, No. 32.
Yusupov, M.M. et al., "Crystal structure of the ribosome at 5.5 A resolution" Science (May 4, 2001) pp. 883-896, vol. 292.
Zhou, Z. et al., "Genetically encoded short peptide tags for orthogonal protein labeling by Sfp and AcpS phosphopantetheinyl transferases" ACS Chem Biol (2007) pp. 337-346, vol. 2, No. 5.
Zhou, Z. et al., "An eight residue fragment of an acyl carrier protein suffices for post-translational introduction of fluorescent pantetheinyl arms in protein modification in vitro and in vivo" J. Am. Chem. Soc. (2008) pp. 9925-9930, vol. 130.
Zhao, Y.Z. et al., "Single-molecule dynamics of gating in a neurotransmitter transporter homologue" Nature (May 2010) pp. 188-193, vol. 465.
Kim, S. et al., "Cloning, Overexpression and Purification of Bacillus subtilis Elongation Factor Tu in *Escherichia coli*" Molecules and Cells (2000) pp. 102-107, vol. 10, No. 1.
International Search Report dated Sep. 13, 2012 issued in International Application No. PCT/US2012/032601, previously submitted on Oct. 7, 2013.

\* cited by examiner

A

B

SIGNAL AMPLIFICATION METHODS FOR THE IMAGING OF PROTEIN SYNTHESIS AND NEUROTRANSMITTER TRANSPORT

CROSS-REFERENCE TO RELATED APPLICATIONS

This application claims priority from U.S. Provisional Application No. 61/472,489, filed Apr. 6, 2011, which is herein incorporated by reference in their entirety.

GOVERNMENT FUNDING

This invention was made with government support under grant number RO1GM079238 awarded by the National Institutes of Health General Medicine. The United States Government has certain rights in the invention.

FIELD OF THE INVENTION

The present invention describes the synthesis of biological samples that can be used for the purpose of enhancing the signal-to-noise ratios achievable during the imaging of protein synthesis, amino acid transport and neurotransmitter transport, particularly in applications where single-molecule resolution is demanded. The present invention provides quencher-labeled elongation factor-Tu (EF-Tu) and fluorophore-labeled tRNA. When these molecules are present in a ternary complex with GTP, the fluorescently-labeled tRNA is quantitatively (or nearly quantitatively) quenched. Once the tRNA is incorporated into an actively translating ribosome, however, a burst of fluorescence is released and can be detected by a variety of techniques, including smFRET imaging. The invention further provides novel EF-Tu constructs for achieving quencher labeling at high levels while retaining native or near native activity in the translation reactions, as well as methods for preparing stable ternary complexes, methods of protein sequencing, methods of detecting amino acid transport using a proteoliposome assay system and the proteoliposomes systems and methods of imaging translation events in single living cells. The present invention should have an immediate impact on next-generation sequencing technologies and the detection of neurotransmitter transporter activities in both in vitro and in vivo settings, a critical component of drug activity/screening assays targeting this important class of molecules.

BACKGROUND OF THE INVENTION

Translation, the process of protein synthesis, follows a universally conserved mechanism that is central to gene expression. Translation is highly regulated in human cells and loss of translation control is a key determinant of cancerous cell growth. Bacterial translation is targeted by a broad array of clinically-important therapeutic compounds that are used to combat infectious disease. However, resistance to known antibiotics is increasingly widespread. The ribosome is the principal component of the cellular translation apparatus and is the integration point for regulation.

The molecular mechanisms of ribosome regulation and antibiotic action remain poorly understood. To catalyze protein synthesis, the ribosome, a highly-conserved, RNA-protein assembly, works in concert with numerous RNA ligands and protein translation factors to convert a messenger RNA (mRNA) template into a specific polypeptide sequence. The mechanism of protein synthesis hinges on repetitive processes central to which is the incorporation of specific, aminoacylated transfer RNA (aa-tRNA) molecules for each mRNA codon, followed by movement of the ribosome along mRNA in discrete, codon steps. As we have demonstrated through our previous research, transient factor binding events and conformational changes in the ribosome are critical to the mechanism of this directional, high-fidelity process.

Messenger RNA (mRNA)-directed protein synthesis takes place on the two-subunit ~2.4 MDa ribosome particle (70S in bacteria) during the elongation phase of translation. In this process, the ~25 KDa, L-shaped aminoacyl-transfer RNA (aa-tRNA) molecule binds the ribosome within the aminoacyl (A) site through base pairing interactions with the mRNA codon within the small subunit (30S) decoding site (Ramakrishnan 2002; Yusupov 2001). The ribosome's recognition of the helical geometry arising from the paired mRNA codon and tRNA anticodon stimulates conformational events in the particle and tRNA that facilitate delivery of the amino acid linked to the distal 3'-CCA terminus of aa-tRNA into the peptidyltransferase center (PTC) of the large subunit (50S) more than 80 Å away (Ramakrishnan 2002; Ogle 2003; Schuette 2009; Villa 2009; Schmeing 2009a, 2009b; Rodnina 2009). The selection process terminates with peptide bond formation catalyzed by elements of the PTC. The mechanism of aa-tRNA selection establishes the genetic code by ensuring that correct (cognate) aa-tRNA are rapidly incorporated into the ribosome while near- and non-cognate aa-tRNAs are rapidly and efficiently rejected (Parker 1989; Rodnina 2005). In vivo and in vitro measurements estimate the rate of translation at ~2-20 amino acids per second with error frequencies ranging from $\sim 1\times 10^{-2}$-$10^{-6}$ depending on experimental conditions (Parker 1989; Johansson 2008; Ninio 2006).

A deeper understanding of the nature, role and timing of factor and tRNA binding events on the ribosome, as well as conformational events within components of the system underpinning rate-determining steps in the process are necessary to gain insight into translation regulation, and for drug screening assays aimed at targeting the translation apparatus for the therapeutic treatment of infection and cancer. Historically, bulk biochemical and biophysical experiments have been employed with the goal of obtaining such information. However, such efforts are hampered by the asynchronous nature of translation events and ensemble averaging phenomena that ultimately compromise quantitative analyses and interpretations. Studies performed in bulk also have been hampered by the need for milligram quantities of pure, highly-active components, which can really only be achieved for relatively simple, non-pathogenic strains of *Escherichia coli* (*E. coli*). As a result, a paucity of quantitative information is available for processive translation reactions for even the most simple, model organisms (e.g., *E. coli*) and almost no information whatsoever regarding the human translation apparatus—from which to advance therapeutic approaches to cancer treatment focused on targeting the translation machinery.

Recent advances in methods that enable the direct imaging of translation reactions using single-molecule fluorescence and fluorescence resonance energy transfer (FRET) overcome many of the aforementioned challenges. However, investigations of single-round and processive translation reactions can be hampered by the need to perform such experiments using relatively high concentrations of fluorescently labeled translation components in solution. Elevated concentrations of fluorescent components in solution cause unwanted background and a global deterioration of signal-to-noise ratios for the types of imaging platforms/strategies presently available including, for example, total internal reflection microscopy, confocal imaging and zero-mode waveguide directed imaging platforms such as those offered by Pacific Biosciences (Menlo Park, Calif.). Such considerations have proven to be a bottleneck for this important area of research and to overcome this limitation, the imaging of protein synthesis reactions must typically be performed using relatively low concentrations of fluorescently labeled translation components (1-200 nM). Such low concentrations hamper translation rates and lead to undesirable side reactions and fluorophore photobleaching, ultimately limiting the utility and interpretation of the measurements. Even the use of zero-mode waveguides, designed specifically to enable the use of higher concentrations of fluorescent components in solution, have failed to effectively overcome this obstacle.

In previous work, we aimed to diminish the negative consequences of unwanted fluorophore photobleaching through the design and synthesis of long-lasting and non-blinking fluorescent dye molecules. However, such compounds do not overcome the issues of background introduced by the use of high concentrations of fluorescent species needed for imaging experiments. Thus, forward progress in the field requires solutions that specifically address the need to use high concentrations of fluorescent agents in solution.

The present invention builds on previous technologies employed most visibly in the field of molecular beacons, which have been used to overcome similar hurdles in the imaging of biological systems using fluorescent probes. Molecular beacons are single-stranded oligonucleotide hybridization probes that form a stem-and-loop structure with a fluorophore covalently linked to the end of one arm and a quencher covalently linked to the end of the other arm. In the absence of targets, the probe is dark, because the stem places the fluorophore so close to the non-fluorescent quencher that they transiently share electrons, eliminating the ability of the fluorophore to fluoresce. When the probe encounters a target molecule, it forms a probe-target hybrid that is longer and more stable than the stem hybrid. Such technology has engendered success in numerous applications, including the in vivo imaging of specific mRNA templates. Proximal quenching hinges on the transfer of energy through space from an excited (illuminated) fluorophore to a neighboring fluorophore that dissipates energy through non-fluorescing pathways (e.g. heat dissipation).

The present invention takes analogous approach to image translation events based on the principle that aminoacyl-tRNA (aa-tRNA) substrates are delivered to the ribosome in a "ternary complex" of elongation factor Tu (EF-Tu), aa-tRNA and GTP, which with labeling in accordance with the present invention, provides "dark" ternary complexes that only fluoresce upon delivery of the charged tRNA to the ribosome and dissociation of the ternary complex.

In previous research, fluorescently labeled tRNA was used to directly monitor translation reactions and drug activity on the ribosome. In the present invention, we describe methods developed to enable attachment of "quencher" fluorophores directly to EF-Tu in a manner that efficiently quenches the fluorophore linked to tRNA when they are bound together in a ternary complex by virtue of the fluorophore and quencher proximity, without compromising the biological activity of the ternary complex in any detectable manner. While originally developed as a means to monitor FRET within ternary complex and conformation changes therein during the delivery of aa-tRNA to the ribosome, we have since simplified this approach on the basis of efforts that enable the direct monitoring of the sequential tRNA incorporation reactions.

No fluorescence-based methods or assays to monitor the kinetic parameters of ternary complex formation and/or dissociation are currently available. In 1985, there was a report of a fluorescence-based assay for ternary complex formation using tRNA$^{Phe}$ labeled at the naturally occurring 4-thiouriding residue at position 8 of tRNA (Abrahamson 1985). However, this assay suffers from relatively poor activity of the components. In particular, the use of tRNA$^{Phe}$ labeled at the 4-thiouridine residue at position 8 suffers from reduced rates of aminoacylation which precludes robust kinetic studies of the process. It also does not employ fluorescently-labeled or quencher-labeled EF-Tu species. In 2010, there was a report published claiming a method for detecting FRET between EF-Tu and tRNA for purposes related to the detection of translation (Perla-Kajan 2010). However, the approach described the introduction of mutations in EF-Tu and a labeling approach that rendered EF-Tu all but inactive for ternary complex formation.

The present invention is unique as it employs novel derivatives of EF-Tu and tRNA where both species can be quantitatively labeled while remaining fully active in translation.

SUMMARY OF THE INVENTION

The present invention is directed to a composition comprising elongation factor-Tu (EF-Tu), wherein at least 80% of said EF-Tu is labeled with a fluorophore or a fluorescence quencher. The label can be attached to a C-terminal tag or other tag. These compositions can further comprise purified EF-Ts.

Another aspect of the invention relates to an expression vector comprising a nucleic acid encoding an EF-Tu having an removable, N-terminal affinity tag operably linked to the EF-Tu coding sequence and an operably-linked C-terminal tag for attachment of a fluorophore or fluorescence quencher. In a preferred embodiment the affinity tag is His-6 followed by EF-Tu coding sequence by a TEV protease cleavage site. One plasmid containing such a construct is the vector is pPROEX HTb-C-termSFP-EF-Tu.

Yet another aspect of the invention provides a composition comprising EF-Ts and a stable ternary complex of EF-Tu labeled with a quencher, GTP and an aminoacylated tRNA (aa-tRNA) labeled with a donor fluorophore, wherein said quencher is in sufficient proximity to said donor fluorophore to form a quenched ternary complex. Such labeling can be done without perturbing the overall nature or kinetics of ternary complex formation. In one embodiment the quencher is Cy5Q and said donor fluorophore is Cy3.

Further still, the invention provides methods of generating stable ternary complexes by (a) providing EF-Tu, EF-Ts, GTP and aa-tRNA; (b) allowing stable ternary complexes to form; (c) isolating said ternary complexes in admixture with said EF-Ts. In some embodiments, EF-Tu has a tag for addition of a quencher and the method further comprises reacting the ternary complex with a quencher for attachment to said EF-Tu.

Another aspect of the instant invention is directed to methods for determining the sequence of a protein by (a) initiating translation of mRNA on surface-immobilized ribosomes under conditions allow single-molecule imaging; (b) conducting in vitro translation with aa-tRNA labeled with a donor fluorophore in a ternary complex with GTP and EF-Tu labeled with a quencher, wherein a different fluorophore is provided for each distinct amino acid-bearing class of aatRNA; (c) detecting fluorescence signals as each amino acid is added to the nascent peptide chain and correlating each signal with a given amino acid to thereby ascertain the sequence of amino acid addition and the sequence of a protein encoded by said mRNA. In this method, the ribosomes can be immobilized for detection via total internal reflection microscopy, confocal imaging or a zero-mode waveguide directed imaging platform. The fluorescence signals can be changes in FRET signals.

Yet a further aspect of the invention provides proteoliposome vesicles which comprise a transmembrane amino acid transporter capable of transporting one or more amino acids into the lumen of said vesicle and which have an amino acid transport-detecting solution encapsulated by the vesicles. Such a solution comprising quencher-labeled EF-Tu-, EF-Ts, GTP, ATP, an aminoacyl tRNA synthetase and its cognate donor fluorophore-labeled tRNA so that the synthetase is capable of acylating its cognate said tRNA upon transport of the appropriate cognate amino into the vesicle. In one embodiment, the transporter is LeuT, the synthetase is LeuRS and the tRNA is a tRNA$^{Leu}$. For some embodiments, the vesicles can have an immobilization tag such as a biotinylated lipid, or a histidine tag on the N or C terminus of said transporter.

These vesicles can be used in further embodiments of the invention that provide methods to detect amino acid transport by immobilizing the vesicles of the invention on a surface suitable for single-molecule imaging; (b) providing an amino acid for transport into the lumen of the vesicles, again the amino acid being suitable for acylation of the tRNA by its cognate synthetase; and (c) detecting ternary complex formation by single-molecule FRET imaging techniques. These methods can further comprise (a) providing a test compound with the amino acid and (b) detecting whether the test compound reduces FRET events relative to control, wherein a reduction of in FRET indicates that the test compound blocks transport activity of said transporter. Any of the imaging techniques described herein can be used, including without limit, total internal reflection microscopy, confocal imaging or a zero-mode waveguide directed imaging.

Another aspect of the invention is directed to an in vitro translation mixture comprising quencher-labeled EF-Tu and fluorophore-labeled tRNA in a ternary complex with GTP. This mixture can also include purified EF-Ts.

Yet a further aspect of the invention is directed to methods of imaging translation events in a living cell by (a) fixing a living cell to a solid surface suitable for single-molecule FRET; (b) microinjecting a ternary complex of quencher-labeled EF-Tu, fluorophore-labeled tRNA and GTP into said cell; and (c) imaging said translation events by smFRET. In some instances, the method includes imaging in the presence of a microtubule disruptor such as taxol.

Additional compositions of the invention include compositions comprising purified EF-Tu having native activity and purified EF-Ts. In such compositions, EF-Tu can be labeled with a fluorophore or a quencher, and can further contain GTP and a labeled or unlabeled tRNA or aa-tRNA. For example, in some embodiments, the tRNA label is a fluorophore when EF-Tu is labeled with a quencher or the label is a quencher when EF-Tu is labeled with a fluorophore.

Further aspects of the invention provide methods to isolated and stabilize EF-Tu which comprises (a) expressing EF-Tu having a removable purification tag ("tagged EF-Tu") in a bacterial cell from a recombinant expression vector; (b) lysing said cells and recovering a soluble fraction containing said tagged EF-Tu; (c) isolating said tagged EF-Tu from said soluble fraction using a purification material for said the tag and recovering said tagged EF-Tu from said material; (d) admixing isolated EF-Ts to said tagged EF-Tu to form an EF-Tu/EF-Ts complex; (e) isolating said complex; (f) optionally, labeling EF-Tu in said complex with a fluorophore or a quencher and separating said unreacted fluorophore or quencher from said complex; (g) removing said purification tag and recovering said complex. In some embodiments, the removable purification tag is a histidine tag, a myelin binding protein tag, a SUMO tag or a polylysine tag and the tagged EF-Tu can have a second tag for labeling with fluorophore or quencher.

A still further aspect of the invention relates to methods of identifying ternary complex inhibitors by (a) providing a pre-formed ternary complex under saturating GTP conditions in the presence of EF-Ts with at least one of EF-Tu or aminoacylated-tRNA (aa-tRNA) fluorescently labeled; (b) adding a test compound to said complex; and (c) monitoring the changes in relative fluorescence, wherein a decrease in relative fluorescence indicates said test compound is a ternary complex inhibitor. Alternatively, the methods of identifying ternary complex inhibitors can be conducted by (a) providing a pre-formed ternary complex under saturating GTP conditions in the presence of EF-Ts with at quencher-labeled EF-Tu and a fluorescently-labeled aminoacylated-tRNA (aa-tRNA) or with fluorophore-labeled EF-Tu and quencher-labeled aminoacylated-tRNA (aa-tRNA); (b) adding a test compound to said complex; and (c) monitoring the changes in relative fluorescence, wherein an increase in relative fluorescence indicates said test compound is a ternary complex inhibitor. For either of these methods, the preformed-complex can be is formed by providing EF-Tu as an EF-Tu/EF-Ts complex.

DETAILED DESCRIPTION OF THE INVENTION

Figure 1:
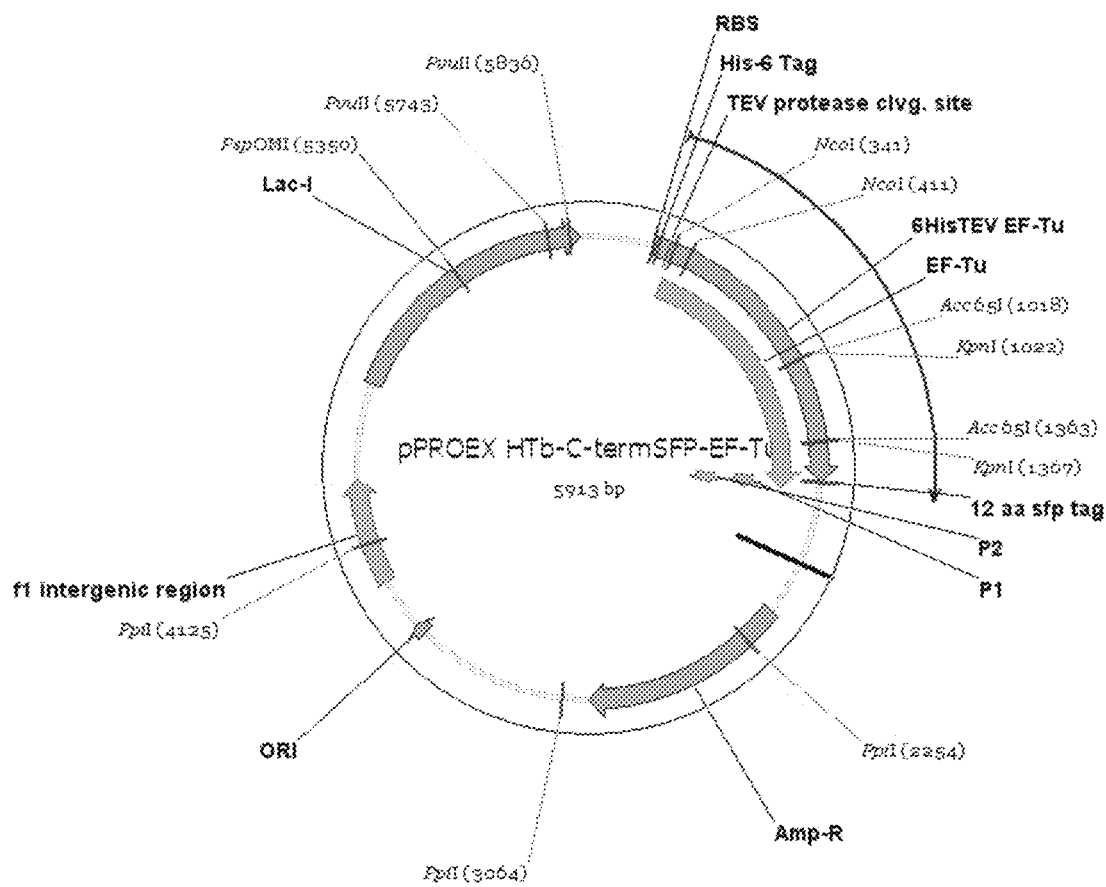
FIG. 1 illustrates an expression vector used for the purification of highly active, fluorescently labeled *E. coli* EF-Tu and a graphical representation of the protein expressed from this vector including the universally conserved domain organization of EF-Tu, the specific sites of tagging shown here to support fluorescent labeling, purification and full activity in ternary complex formation and translation. The precise amino acid sequence generated from this construct is in the specification.
Figure 1:
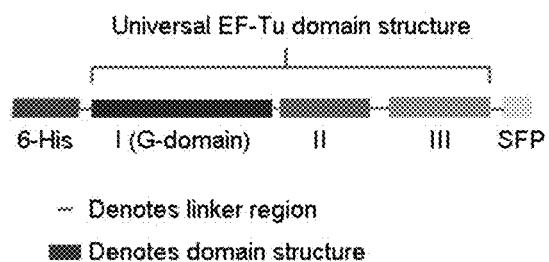

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

DEFINITIONS

As used herein, "quencher-bound EF-Tu," "EF-Tu-quencher," and "EF-Tu labeled with a fluorescence quencher" are interchangeably used to mean elongation factor-Tu from a bacterial species which has a quencher molecule attached so that when such EF-Tu is present in a ternary complex with GTP and an aminoacylated-tRNA, which itself has a covalently attached donor fluorophore, the ternary complex does not exhibit fluorescence above background levels. In general, such EF-Tu molecules retain native translational elongation activity. The EF-Tu of the invention can be from a bacterial or mammalian source. The mammalian equivalent of EF-Tu is also known as eEF-1α.

As used herein, a "quencher" is a molecule or a moiety (i.e., group) that has the ability to alter the photophysical properties of a fluorophore, particularly by altering the light state-dark state (i.e., singlet-triplet) occupancy distribution or relaxation pathway of excited and relaxing electrons. The quenchers of the present invention are also referred to herein as acceptor fluorophores. Quenchers are well known in the art.

As used herein, a "fluorophore" (or "fluorescing species") refers to any species possessing a fluorescent property when appropriately stimulated. The stimulation that elicits fluorescence is typically illumination; however, other types of stimulation (e.g., collisional) are also considered herein.

Fluorophores are well known in the art. Hence in one embodiment, the fluorophore is an organic fluorophore. In some embodiments, the organic fluorophore is a xanthene derivative (e.g., fluorescein, rhodamine, Oregon green, eosin, and Texas Red), cyanine or its derivatives or subclasses (e.g., streptocyanines, hemicyanines, closed chain cyanines, phycocyanins, allophycocyanins, indocarbocyanines, oxacarbocyanines, thiacarbocyanines, merocyanins, and phthalocyanines), naphthalene derivatives (e.g., dansyl and prodan derivatives), coumarin and its derivatives, oxadiazole and its derivatives (e.g., pyridyloxazoles, nitrobenzoxadiazoles, and benzoxadiazoles), pyrene and its derivatives, oxazine and its derivatives (e.g., Nile Red, Nile Blue, and cresyl violet), acridine derivatives (e.g., proflavin, acridine orange, and acridine yellow), arylmethine derivatives (e.g., auramine, crystal violet, and malachite green), and tetrapyrrole derivatives (e.g., porphyrins and bilirubins). Some particular families of dyes considered herein are the Cy® family of dyes (e.g., Cy2, Cy3, Cy3B, Cy3.5, Cy5, Cy5.5, and Cy7), the Alexa® family of dyes (e.g., Alexa Fluor 350, 405, 430, 488, 500, 514, 532, 546, 555, 568, 594, 610, 633, 647, 660, 680, 700, 750, and 790), the ATTO® family of dyes (e.g., ATTO 390, 425, 465, 488, 495, 520, 532, 550, 565, 590, 594, 601, 615, 619, 629, 635, 645, 663, 680, 700, 729, and 740), and the Dy® family of dyes (e.g., DY 530, 547, 548, 549, 550, 554, 556, 560, 590, 610, 615, 630, 631, 631, 632, 633, 634, 635, 636, 647, 648, 649, 650, 651, 652, 675, 676, 677, 680, 681, 682, 700, 701, 730, 731, 732, 734, 750, 751, 752, 776, 780, 781, 782, and 831). The ATTO dyes, in particular, can have several structural motifs, including, coumarin-based, rhodamine-based, carbopyronin-based, and oxazine-based structural motifs. Additional fluorophores, for example, are disclosed in WO2010/096720, published Aug. 26, 2010.

EF-Tu Quencher

The present disclosure describes methods for site-specifically labeling both aa-tRNA and EF-Tu molecules with donor and acceptor fluorescence dyes, respectively, where the acceptor fluorophore is specifically of the "quencher variety" so that the fluorescence emanating from fluorescently labeled aa-tRNA is highly quenched while it is bound in ternary complex. The basic principle of the approach hinges on the established mechanism of translation where at the commitment stage of the multistep aa-tRNA selection process, EF-Tu hydrolyzes GTP and donates aa-tRNA to the codon-programmed decoding site of the ribosome when the correct tRNA is present. Background fluorescence, the limiting issue for single-molecule imaging, is absent or highly reduced even at high concentrations of ternary complex. GTP hydrolysis by EF-Tu results in EF-Tu's dissociation from the ribosome thereby leading to its separation from aa-tRNA and a corresponding loss of quenching and a corresponding burst of fluorescence as the aa-tRNA enters the ribosome. As translation fidelity in this step is estimated to be between $10^{-3}$-$10^{-4}$, bursts of fluorescence are very unlikely to occur unless the aa-tRNA corresponds to the mRNA codon being "read" by the ribosome. Bursts of donor fluorescence can be detected by time-correlated photon counting instruments such as avalanche photodiode or other detection devices such as EMCCDs. When one or more quenched ternary complexes are added to an in vitro translation mixture along with all of the other molecular components necessary for protein synthesis, individual aa-tRNA incorporation events can be temporally and spatially identified according to the frequency of light emitted, which can in principle be made distinct for each specific tRNA in the milieu. Such systems can, for example, be leveraged to monitor the rate of misincorporation of aa-tRNA if the reaction milieu contains a fluorescently-labeled tRNA that is not encoded by the mRNA being read by the ribosome. Thus, when imaging translation processes using total internal reflection (TIRF) microscopy and/or zero-mode waveguides implemented on in-house constructed and/or Pacific Biosciences sequencing instruments, high-concentrations of ternary complexes can be used in solution to enable biologically relevant (fast) rates of protein synthesis.

The present invention also entails the cloning and purification of highly active genetic derivatives of EF-Tu (or its homologue depending on the organism) from living organisms such as bacteria, insect cells, yeast or human tissue culture. The requirement to obtain highly purified material is aided by the introduction of epitopes for affinity purification (e.g. poly-histidine tagging). The need to fluorescently label EF-Tu (or its homologue depending on the organism) requires the introduction of one or more tagging strategies that allows for the near quantitative or quantitative coupling of the protein to the desired fluorophore/quencher in a manner that does not affect function (either via the labeling method or as a consequence of the fluorophore/quencher being introduced). The types of labeling strategies typically center on the labeling of site-specifically introduced cysteine residues, which can be coupled to sulfur-reactive fluorophores (e.g. maleimide linked), in an otherwise cysteine free background. As described below, this turns out to be a major limiting factor for many proteins as they often contain native cysteine residues that are important to function. To date, the vast majority of functional translation studies have been performed using the components of specific, non-pathogenic laboratory strains of E. coli. Thus, we have focused our efforts to demonstrate the proof-of-principle for this approach and reduction to practice using similar components. EF-Tu contains three native cysteine residues, two of which are critical to function, making alternative labeling strategies imperative. While a tag can be introduced in any number of solvent accessible regions of the protein that are not conserved and distal to the active sites for tRNA and GTP binding, our initial efforts have focused inserting a tag on the C-terminus of EF-Tu, which meets all of these criteria and is also very close to the site of labeling on tRNA within ternary complex (FIG. 1). The amino acid sequence of a useful EF-Tu of the present invention is provided below:

(SEQ ID. NO. 1)
MSYYHHHHHHDYDIPTTENLYFQGAMGSKEKFERTKPHVNVGTIGHVDHGKTTLT

AAITTVLAKTYGGAARAFDQIDNAPEEKARGITINTSHVEYDTPTRHYAHVDCPGH

ADYVKNMITGAAQMDGAILVVAATDGPMPQTREHILLGRQVGVPYIIVFLNKCDM

VDDEELLELVEMEVRELLSQYDFPGDDTPIVRGSALKALEGDAEWEAKILELAGFL

DSYIPEPERAIDKPFLLPIEDVFSISGRGTVVTGRVERGIIKVGEEVEIVGIKETQKSTC

TGVEMFRKLLDEGRAGENVGVLLRGIKREEIERGQVLAKPGTIKPHTKFESEVYILS

KDEGGRHTPFFKGYRPQFYFRTTDVTGTIELPEGVEMVMPGDNIMVVTLIHPIAMD

DGLRFAIREGGRTVGAGVVAKVLSGDSLSWLLRLLN.

The amino acid sequence of the SFP tag is GDSLSWLL-RLLN (SEQ. ID. No. 2). Fluorophores can be attached to the SFP tag as generally described by Yin 2006. Other tags can be used as well including the 12 amino acid acyl carrier protein tag (AcpS) and a shorter, 8 amino acid tag derived therefrom, both of which are described in Zhou 2008.

Further tags for enzymatic labeling include ACP, Q-tag (for example Q3: NH2-GQQQLG-COOH) transglutaminase-catalyzed site-specific conjugation of small-molecule probes to proteins in vitro and on the surface of living cells and FGE-tag (for example: LCTPSR (wild-type), LCTASR, and LCTASA) (Rush 2008). Peptidyl affinity tags that can be used for purification include, but are not limited to, Sumo, Glutathione S-transferase (GST), His6, His10 and Flag.

This construct organization yields an EF-Tu molecule that has been shown to be fully active in ternary complex formation and translation and can be quantitatively labeled with any number of synthetically prepared or commercially available fluorophore species.

However, other organizations of the construct which retain "full" activities are also envisaged, wherein the SFP and affinity tags are moved either into, or between, EF-Tu domains by molecular cloning and site directed mutagenesis strategies. Notably, where such manipulations initially introduce negative functional consequences, such defects can be ameliorated by directed evolution of the protein construct via established means (e.g. site-directed mutagenesis or PCR mutagenesis strategies) using the ternary complex formation and protein synthesis assays as a guide for function. Such efforts may include the construction of "heterologous" forms of EF-Tu, where individual elements or domains of the protein are swapped for analogous elements or domains of EF-Tu from other species. Labeled within the SFP tag at the C-terminal domain of EF-Tu, we have shown that a single site of fluorophore labeling is sufficient to achieve almost complete quenching of tRNA within ternary complex. For sites more distal to the fluorophore linked to the tRNA molecule, multiple sites of labeling within EF-Tu could enable an equivalent level of quenching. Enzymatic approaches have the distinct advantage over alternative strategies for the introduction of fluorophores into proteins via non-cysteine methods, as they have the potential to enable the quantitative labeling of EF-Tu under conditions where EF-Tu remains stable (the "Tu" of EF-Tu is an acronym for "temperature unstable" as EF-Tu tends to aggregate/unfold if handled improperly or over extended periods at ambient temperatures). Such considerations have been shown to be a major determinant of the success of the proposed strategies. Some initial experiments introducing fluorophores into EF-Tu following non-natural amino acid chemistry needed to be performed at relatively low pH values (e.g. pH 5.5 or below) and were highly inefficient, leading the majority of EF-Tu to aggregate during the labeling reaction.

Ternary Complex Isolation

A major advance came with the inclusion of Elongation Factor-Ts (EF-Ts) in our reactions. EF-Ts is a guanosine nucleotide exchange factor, which is thought to operate on the GDP-bound form of EF-Tu generated subsequent to aa-tRNA entry into the ribosome, in order to mediate rapid nucleotide exchange to its GTP bound form, which is then competent for ternary complex formation (EF-Tu-GDP has almost no affinity to aa-tRNA). As had been previously shown and utilized for crystallographic determination efforts, EF-Ts forms a tight, binary complex with EF-Tu, and although to our knowledge it had not been previously identified as being advantageous for such purposes, we have shown that inclusion of EF-Ts during the isolation of EF-Tu from the cell and during EF-Tu's fluorescent labeling dramatically aids in overcoming the inherent instability of EF-Tu, Indeed, EF-Tu is so unstable in the absence of EF-Ts that even when EF-Tu is stored, in a highly purified form, it is prone to losses in activity (e.g. ternary complex formation, aggregation and degradation. Such features of EF-Tu have significantly hampered previous research in this area. When EF-Tu is stored as a binary complex with EF-Ts, we have shown that EF-Tu remains stable for at least three years, when stored at −20° C. in 50% glycerol. EF-Ts also appears to aid ternary complex formation by acting as a chaperone of the process to accelerate both the formation and breakdown of ternary complex.

Accordingly, the present invention provides a composition comprising elongation factor-Tu (EF-Tu), wherein at least 80% of the EF-Tu is labeled with a fluorescence quencher. Levels of 85, 90, 95, 98, 99 and essentially 100% labeling are commonly achieved with this method.

For the tRNA species of the reactions, the donor fluorophore can be site-specifically attached, for example, to naturally occurring post-transcriptionally modified nucleotides (e.g. s4U8, acp3U47, dihydrouridine16/17/20). However, other methods and sites of labeling may also be used, including ligation strategies and/or the preparation of synthetic tRNAs by chemical means, where reactive groups can be introduced site-specifically into the tRNA molecule.

In an initial approach, FRET was to be observed between a "donor" labeled tRNA molecule and "acceptor" labeled EF-Tu molecule using traditional fluorophore pairs (Cy3/Cy5 and/or Alexa 555/Alexa 647), where fluorophores were introduced into EF-Tu using the methods of non-natural amino acid incorporation as originally described by Schultz and co-workers. However, we learned through these and related investigations that the most efficient and effective way of introducing fluorophores into EF-Tu was via newly established enzymatic labeling approaches, which can be used to incorporate fluorophores into 6-12 amino acid epitope tags introduced into a protein of interest as described for example in Yin 2006.

These findings lead us to the conclusion that "quenched" ternary complexes can be prepared, isolated and stored, as described above, for later use following the aforementioned procedures, where unique fluorophore pairs can be utilized for each individual ternary complex isoforms, which bear the acp3U47 residue (e.g. those containing tRNA$^{Phe}$, tRNA$^{Lys}$, tRNA$^{Val}$ etc.), to enable their unambiguous experimental identification using standard optical treatments for detection (such as those employed for three-color FRET experiments recently published by our group. Here, the donor fluorophores used must be properly matched with efficient "quencher" fluorophore species (e.g. Cy2-Cy3Q; Cy3-Cy5Q; Cy5-Cy7Q etc). Where specific fluorophore quenching molecules of the Cyanin family are not readily available, quencher dyes such as "Black Hole Quenchers or QSY can be used or new quencher species can be synthesized. Notably, the number of distinctly "colored" tRNAs can be expanded beyond the simple "one dye-one quencher" format by including more than one dye type on each tRNA and/or more than one type of quencher on EF-Tu protein, conceivably allowing each tRNA isoform present in the cell to be uniquely "marked". Our experiences with enzymatic labeling strategies have demonstrated that a broad variety of "quencher" fluorophores can be efficiently incorporated. For tRNA molecules that do not contain the acp3U47 residue, alternative sites of labeling, which we and others have shown can be site-specifically labeled with various fluorophore species without significant loss of translation activity. For instance almost every tRNA species contains either a 4-thiouridine (s4U) residue at position 8 or a dihydrouridine residue at position 16, 17 or 20 (sometime both), which can be labeled with sulfur-reactive or nucleophilic groups linked to fluorophore species, respectively. While C-terminal labeling of EF-Tu is still expected to result in efficient quenching of dyes linked to these positions of tRNA, further quenching to reduce fluorescence intensity can be achieved by the introduction of additional sites of "quencher" labeling within the EF-Tu protein according to the aforementioned criteria.

The nature and stability of ternary complex can be "tuned" for the performance desired using activity assays as a guide for directed evolution of the system. For instance, if a more stable ternary complex is desired, the affinity of EF-Tu for aa-tRNA can be increased by 1] mutations in individual domains of EF-Tu or linker domains connecting individual domains; 2] by "swapping individual EF-Tu domains and/or linker regions for those from other species, where increased stability has already been incorporated as an evolved feature of the system (e.g. thermophilic organisms). The sequence of tRNA can also be varied through analogous strategies, which are largely described in the literature. Such tuning may be particularly important for translational studies as the affinity of EF-Tu for aa-tRNA plays a central role in the fidelity mechanism and as such, influences the rate and fidelity of aa-tRNA selection. "Evolution" of the ternary complex may also be demanded for alternative embodiments of the inventions described below, where ternary complex resides within a confined environment and where no signal of complex formation is desired in the absence of amino acid.

Uses of the Invention

The present invention can be used for multiple purposes including direct sequencing of mRNA or protein and/or mechanistic investigations. Such technological foundations are also envisaged to enable the direct imaging of sites of local translation in the cell through the introduction of specific sequences of fluorescently labeled aa-tRNAs unique for mRNAs containing unique codon sequences (either natural or genetically introduced).

As described below, the methods described for fluorescence-based detection of ternary complex formation can also be used for the detection of neurotransmitter transporter activity (both in vitro and in vivo) and amino acid transport activity as well as aminoacyl tRNA synthetase activities via coupled reactions using a synthetic biology-like approach.

The neurotransmitter transporter activity assay embodiment of the invention, in its most straightforward implementation, entails the encapsulation of the components required for ternary complex formation (minus the amino acid substrate) inside of a proteoliposome, where the transporter protein, embedded into the lipid bilayer of the same proteoliposomes, mediates the movement of specific substrates (for instance an amino acid) from the extracellular to intracellular milieu, which upon arrival to the lumen of the proteoliposomes becomes enzymatically linked to the 3'-terminus of tRNA (a reaction termed "charging" carried out by specific aminoacyl-tRNA synthetases), which thereby enables ternary complex to form resulting in either the appearance or disappearance of fluorescence depending on the fluorophore pair linked to tRNA and EF-Tu in the experiment. While such assays may initially be limited to the sub-set of neurotransmitter transporters that mediate the reuptake of amino acids from the extracellular milieu, one can also envisage based on previously established protocols, the directed evolution of aminoacyl-tRNA synthetases for the purpose of detecting the transport of non-amino acid substrates using an analogous approach, for substrates such as dopamine, serotonin etc. The fundamental basis of the proposed assay has been demonstrated through both bulk and single-molecule in vitro assays using components of the *E. coli* translation apparatus (as described below). Notably, the aforementioned approach inherently probes for the activity of aminoacyl tRNA synthetases. Thus, another embodiment of this invention is to use the signal resulting from the formation of ternary complex as a means of probing the activities of aminoacyl tRNA synthetases, a broad class of diverse proteins that have therapeutic value due to their conserved and their species specific nature. Such an embodiment may or may not be performed in an encapsulated environment. However, as the mechanism of protein synthesis is conserved across all domains of life, components of other translation systems may also be employed as needed.

The invention can also be used to assay for amino acid-transporting function comprising by providing solution containing liposome with transmembrane amino-acid transporting protein in membrane, inside of which is fluorophore-labelled EF-Tu, EF-ts, GTP, fluorophore-labeled tRNA, and aminoacyltransferase, and ATP; providing amino acids in solution and monitoring FRET events within the liposome. These assays can be configured for single-molecule detection using total internal reflectance microscopy, confocal imaging or ZMW imaging. In some embodiments, a test compound can be added to the assay to evaluate its potential for inhibiting amino acid transport, in which case a reduction in FRET compared to controls indicates that test compound is blocking activity of transporting protein.

One or the other of the EF-Tu or the tRNA may be labeled with a quencher such that a reduction in FRET indicates that amino acid transport has been blocked. The transmembrane amino-acid-transporting protein may be, for example, a member of any of the following families: high affinity glutamate and neutral amino acid transporter; heavy subunits of heteromeric amino acid transporters; cationic amino acid transporter/glycoprotein-associated; proton oligopeptide cotransporter; vesicular glutamate transporter; vesicular amine transporter; some mitochondrial carriers; multifunctional anion exchanger; vesicular inhibitory amino acid transporter; proton-coupled amino acid transporter; System A & N, sodium-coupled neutral amino acid transporter; Vesicular inhibitory amino acid transporter. The transmembrane amino-acid-transporting protein may be a member of the neurotransmitter/sodium symporter family.

For example, the particular transporter can be isolated (from a convenient source, including a recombinant expression source) and reconstituted into proteoliposomes that encapsulate the cognate aminoacyl synthetase and tRNA for the amino acid transport activity to be assayed. In addition, the lipid bilayer can include lipids or other molecules that allow the proteoliposomes to be surface immobilized for conducting the smFRET analysis as taught herein.

Ternary Complex Drug Screening Assay

In bacteria, each isoform of aminoacyl-tRNA (aa-tRNA$^{aa}$) is delivered to the translating ribosome in a ternary complex with elongation factor Tu (EF-Tu) and guanosine nucleotide triphosphate (GTP). Contacts between EF-Tu and tRNA$^{aa}$ are largely conserved between species, where recognition of the aminoacyl moiety is mediated by a binding pocket located between domains 1 and 2 of EF-Tu. Through its interactions with the acceptor arm of tRNA, the GTP-bound form of EF-Tu forms a high-affinity complex with aa-tRNA$^{aa}$, stabilizing the otherwise labile ester linkage between tRNA$^{aa}$ and amino acid from water-mediated hydrolysis.

The position of EF-Tu in ternary complex enables the process of aa-tRNA$^{aa}$ binding to the ribosome to be coupled to GTP hydrolysis. During aa-tRNA$^{aa}$ selection, mRNA codon-tRNA anticodon contacts taking place on the small ribosomal subunit drive EF-Tu to make direct contacts with components of the large ribosomal subunit GTPase Activating Center (GAC). EF-Tu's contacts with the GAC increase the affinity of ternary complex for the ribosome to accelerate the rate of protein synthesis. Moreover, when aa-tRNA$^{aa}$ is correctly positioned, contacts with the GAC are made that strongly stimulate the intrinsic GTPase activity of EF-Tu. Following GTP hydrolysis, EF-Tu undergoes a conformational transition that allows the 3'-aminoacyl terminus of tRNA to accommodate into the peptidyltransferase center (PTC) of the large subunit where peptide bond formation occurs to elongate the nascent peptide chain. While order and timing of structural transitions in EF-Tu that allow its release from aa-tRNA$^{aa}$ release remain unclear, EF-Tu's relatively high affinity for GDP, and the low affinity of EF-Tu•GDP for aa-tRNA$^{aa}$ are the thermodynamic driving forces of ternary complex disassembly following GTP hydrolysis. The recycling of EF-Tu back to its GTP bound form requires the action of Elongation Factor-Ts (EF-Ts), a guanosine nucleotide exchange factor essential to cell growth (Gromadski 2002). Antibiotics that disrupt EF-Tu's interaction with the ribosome or that bind directly to EF-Tu and/or ternary complex are potent inhibitors of translation (Young 2011; Parmeggiani 2006a, b).

Despite its importance as a site of regulation in protein synthesis, kinetic features of ternary complex formation and disassembly are incomplete. Elucidating the biophysical parameters underpinning ternary complex assembly and disassembly can facilitate and expand the repertoire of experiments aimed at exploring the mechanism of aa-tRNA$^{aa}$ selection as well as next-generation processive protein synthesis reactions where fluorescent forms of ternary complex are required (Uemera 2010; Petrov 2011). Accordingly, another aspect of the invention provides a fluorescence-based assay for monitoring ternary complex formation that allows the measurement of new kinetic and thermodynamic features of EF-Tu's interaction with aa-tRNA. In addition, the assay system provides a reliable and quantitative method to study ternary complex-targeting antibiotics. This method is illustrated by experiments to monitor the pre-steady state kinetics of thiazolyl peptide antibiotics and kirromycin with fluorescently-labeled ternary complex. The rates of ternary complex dissociation provide a useful and functional basis to quantify antibiotic efficacy.

Currently, ternary complex is thought to be formed from the dynamic exchange between EF-Tu, GTP, aa-tRNA, and EF-Ts as outlined by the following kinetic reactions (8):

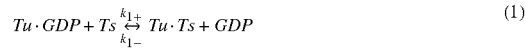

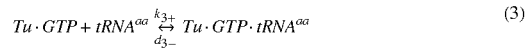

In this model, the role of EF-Ts is to displace GDP from EF-Tu, forcing EF-Tu to adopt a conformation that readily associates with GTP (10). Previous data suggest that the species EF-Tu•GDP•EF-Ts exists transiently in reaction 1 followed by the quick dissociation of GDP (125 s$^{-1}$) (Gromadski 2002). Likewise, in reaction 2, the short lived species EF-Tu•GTP•EF-Ts exists transiently with EF-Ts rapidly leaving (K$_d$=2 µM) (Gromadski 2002). In this way, EF-Ts recycles EF-Tu through intrinsic guanine nucleotide exchange factor activity. Although some kinetic information exists about eq. 3 a complete understanding of the formation and dissociation of ternary complex is lacking.

The data obtained revealed ternary complex formation to be a high-affinity interaction with nanomolar binding affinity. However, contrary to expectations, affinity of the GTP nucleotide for ternary complex was relatively low. These data indicate that an exchange between the nucleotide-bound ternary complex (EF-Tu•GTP•aa-tRNA) and the nucleotide-free binary complex (EF-Tu•aa-tRNA) exists in the absence of GTP hydrolysis. Consistent with this notion, ternary complex can be efficiently dissociated by competing concentrations of GDP. Similarly, gel filtration studies demonstrated that ternary complex could only be efficiently isolated when the GTP nucleotide was present in the running buffer of the experiment. These findings indicate yet unappreciated dynamic features of ternary complex assembly and dissociation that are relevant to the cellular regulation of protein synthesis.

EF-Tu is critical to bacterial protein synthesis and serves as an important target for small-molecule inhibitors. Kirromycin has been identified to target EF-Tu. A powerful application of a pre-steady state kinetic assay of ternary complex is the facility to investigate EF-Tu targeting antibiotics. The data reveal that kirromycin decreases the $k_{off}$ of nucleotide from EF-Tu, having the overall effect of stabilizing ternary complex. This role of kirromycin is congruent with its mode of efficacy in the ribosome. The fluorescent-based approach presented is a useful method for identifying and characterizing ternary complex targeting antibiotics.

Hence a drug screening assay for ternary complex is directed a method of providing a pre-formed ternary complex under saturating GTP conditions in the presence of EF-Ts with at least one of EF-Tu or aminoacylated-tRNA (aa-tRNA) fluorescently labeled, adding a test compound or drug to be screened to said complex and monitoring the changes in relative fluorescence. In this case, a decrease in relative fluorescence indicates that the test compound or drug disrupts the ternary complex and is thus an inhibitor of ternary complex formation. In an alternative format, the assay can use quencher-labeled EF-Tu and fluorescently-labeled aminoacylated-tRNA (aa-tRNA) or fluorophore-labeled EF-Tu and quencher-labeled aminoacylated-tRNA (aa-tRNA) and follow an increase in relative fluorescence to indicate that the test compound is a ternary complex inhibitor. Pre-formed ternary complexes consist of EF-Tu, aa-tRNA and GTP. They can be formed in a stop flow appaturs by adding the components in any order before addition of the drug or test compound. Moreover, in preferred embodiments, the EF-Tu is present or added as an EF-Tu/EF-Ts complex.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. All references patents, patent applications or other documents cited are herein incorporated by reference in their entirety.

Example 1

Preparation of Quencher-Bound EF-Tu, Various Components and General Methods

A. Preparation of Active, Quencher-Bound EF-Tu

EF-Tu from *E. coli* was PCR amplified and cloned into the bacterial expression vector pPROEX-Ht-b through restriction enzyme technologies. This clone includes an N-terminal 6-histidine (6-His) tag separated from the native protein sequence by a TEV protease cleavage site so that both tags can be proteolytically removed from the protein at the appropriate step following purification and fluorescent labeling. Into this clone of EF-Tu, originally described in Blanchard 2004a and Blanchard 2004b, an SFP epitope or sequence tag composed of 12 amino acids on the C-terminus was introduced to produce pPROEX HTb-C-termSFP-EF-Tu (FIG. 1). Fluorescence quenchers are enzymatically coupled to the SFP tag according to the method of Yin 2006.

B. Preparation of tRNA and Ribosomes

Fluorophore-labeled tRNA from *E. coli* was prepared by site-specifically attaching the donor fluorophore to naturally occurring post-transcriptionally modified nucleotides (e.g. s4U8, acp3U47, dihydrouridine16/17/20). Wild-type ribosomes were purified from MRE600 *E. coli* or other lab strains (Blanchard 2004a).

C. Acquisition and Analysis of smFRET Data smFRET data were acquired using a prism-based total internal reflection (TIR) microscope as previously described (Blanchard 2004b). Experiments were performed in Tris-polymix buffer in the presence of an oxygen scavenging environment (1 unit/μl glucose oxidase, 8 units/μl catalase, 0.1% v/v glucose) containing a cocktail of triplet-state quenching compounds (1 mM Trolox, 1 mM cyclooctatetraene, 1 mM nitrobenzyl-alcohol) (Dave 2009). Experiments were performed in the presence of 15 mM Mg(OAc)$_2$ unless otherwise noted. Ribosome complexes were surface immobilized following brief incubation within PEG-passivated, strepatividin-coated quartz microfluidic devices. Cy3 fluorophores were excited by the evanescent wave generated by total internal reflection of a single frequency light source (Ventus 532 nm, Laser Quanta). Cy3 and Cy5 fluorescence traces were collected using a 1.2 NA 60× water-immersion objective (Nikon), where optical treatments were used to spatially separate Cy3 and Cy5 frequencies onto a cooled, back-thinned CCD (Cascade 128, Photometrics). Fluorescence data were acquired using MetaMorph acquisition software (Universal Imaging Corporation) at a rate of 100 frames per second (10 ms integration).

Data analysis was performed using custom software implemented in MATLAB (The MathWorks). Cy3 and Cy5 fluorescence-time traces were extracted from wide-field images by finding peaks of intensity above a defined threshold and summing the 5 most intense pixels proximal to each intensity maximum. Traces were corrected to zero background intensity.

Example 2

Bulk Ternary Complex Analysis

Figure 2:
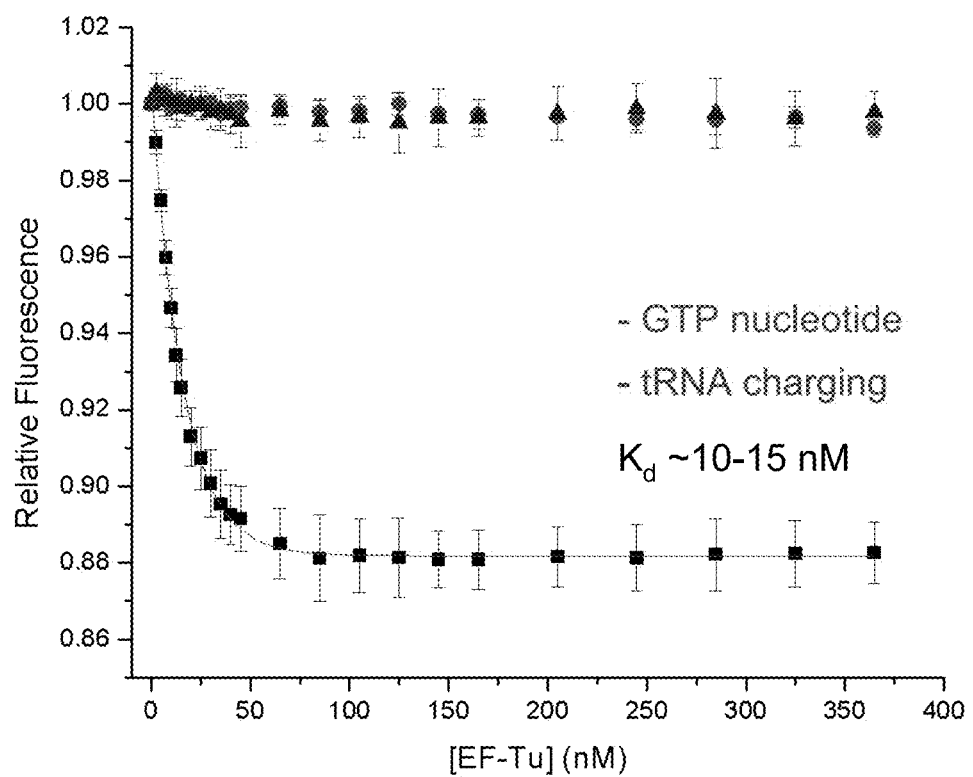
FIG. 2 illustrates the formation of ternary complex using components from *E. coli* showing that complex formation depends strictly on the presence of the aminoacyl group on the 3'-residue of tRNA (resulting from its "charging" by phenylalanyl tRNA synthetase) as well as the GTP molecule. The formation of ternary complex was performed at saturating GTP concentrations, while titrating pure, unlabeled EF-Tu and tracking changes in fluorophore intensity linked to tRNA. Under these experimental conditions, fluorophore intensity decreases as ternary complex is formed (■). The fluorescence intensity in the absence of GTP or tRNA charging is plotted for (▲) and (●), respectively.

Initial experiments focused on the molecular determinants of ternary complex formation in vitro using *E. coli* EF-Tu and tRNA$^{Phe}$. As shown in FIG. 2, a fluorescence based approach was initially developed, whereby the tRNA$^{Phe}$ molecule was fluorescently labeled at position 47 (acp3U47) with a donor (Cy3) fluorophore, which exhibits a change in quantum yield upon ternary complex formation. Depending on the solution conditions of the experiment, the formation of ternary complex can be detected as either a rise or fall in fluorescence intensity depending strongly on the solution conditions of the Cy3 fluorophore linked to tRNA$^{Phe}$. Other tRNA species (e.g., Cy3-labeled tRNA$^{Lys}$) undergo similar changes in fluorescence intensity. These data showed that under the conditions of the experiment, ternary complex formation was strictly dependent on the presence of an aminoacyl moiety at the 3'-terminus of tRNA$^{Phe}$ (resulting from its "charging" by phenylalanyl tRNA synthetase) and GTP. These data also showed a high affinity interaction, consistent with in vivo ternary complex activities (the experimentally derived $K_d$ of EF-Tu's interaction with Phe-tRNA$^{Phe}$ in the presence of saturating GTP (>10 μM) was ≤15 nM). In a reciprocal experiment (FIG. 3), the affinity of GTP in the formation of ternary complex was shown to be approximately 200 nM, by performing the experiment beginning with Phe-tRNA$^{Phe}$ in solution in the presence of saturating EF-Tu concentrations (~300 nM) and), titrating GTP while tracking instead of EF-Tu, to monitor changes in fluorophore intensity linked to tRNA upon ternary complex formation.

Figure 4:
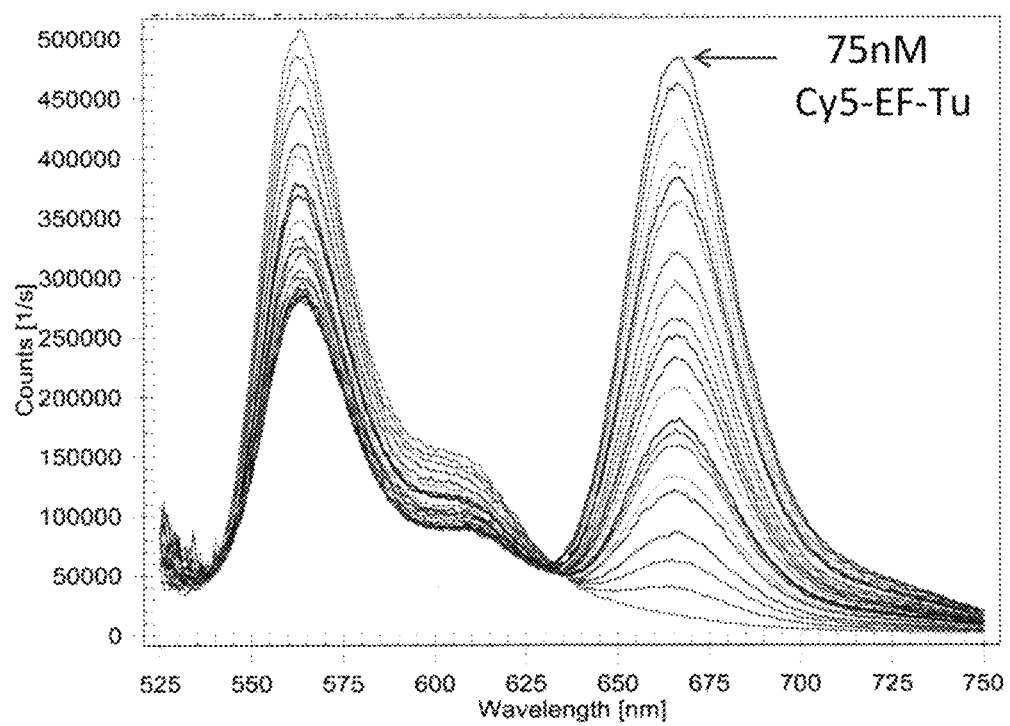
FIG. 4 illustrates a ternary complex formation assay based on the measurement of FRET in bulk solution between Cy5-labeled *E. coli* EF-Tu at the C-terminal SFP tag and Cy3-labeled Phe-tRNA$^{Phe}$ in the presence of saturating GTP concentration ($\geq$10 μM). Each curve in the titration represents a distinct EF-Tu concentration. The apparent affinity of Cy5-labeled EF-Tu for Phe-tRNA$^{Phe}$, determined from the anticorrelated changes in Cy3 and Cy5 fluorescence intensities, is comparable to wild-type EF-Tu. The FRET efficiency between Cy3 and Cy5, although clearly significant, is difficult to determine precisely from the raw, uncorrected data as the detector is relatively insensitive to Cy5 fluorescence frequencies.

Using bulk fluorimetry assays with the same donor-labeled tRNA$^{Phe}$ molecule and EF-Tu enzymatically labeled at its C-terminus through a 12-amino acid "SFP" tag with the Cy5 fluorophore, Cy5 that was fully functional in the ternary complex formation assay, exhibiting a similar titration behavior as indistinguishable from that found when using the "wild-type," native EF-Tu protein, particularly in terms of the apparent affinity of the interaction, as estimated from the mid-point of the anticorrelated changes in Cy3 and Cy5 intensities (FIG. 4). While such assays demonstrated the appearance of substantial FRET upon the formation of ternary complex, determination of the affinity and FRET efficiency of the interaction using this approach was complicated by the nature of the instrumentation used, where the collection efficiency of light emitted by the Cy5 fluorophore is substantially compromised by the instrument's photomultiplier used.

Example 3

FRET Efficiency in Ternary Complex Formation

Figure 5:
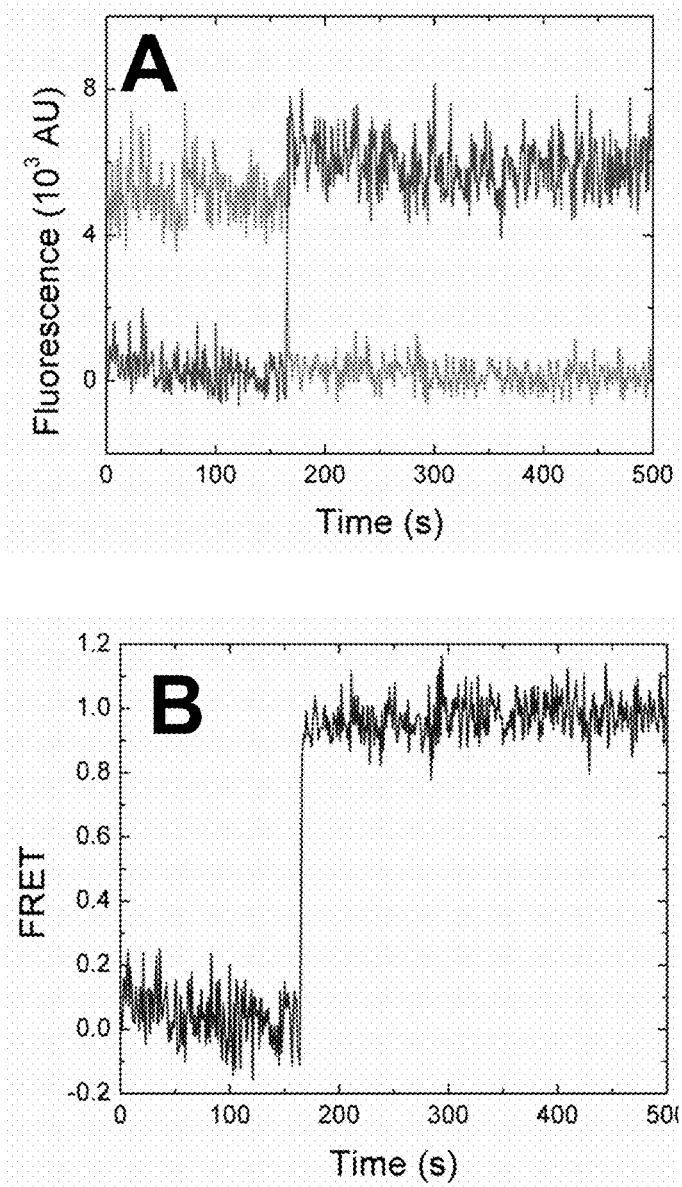
FIG. 5 shows a single-molecule ternary complex formation assay based on the measurement of FRET between surface-immobilized (via an N-terminal 6-His tag), Cy3-labeled E. coli EF-Tu at the C-terminal SFP tag and Cy5-labeled Phe-tRNA$^{Phe}$ in the presence of saturating GTP concentration (≥10 µM). The FRET efficiency of the interaction, determined by the ratio of Cy5 intensity over total intensity, is approximately 1 (the theoretical maximum), indicating a proximity between the Cy3 and Cy5 pair in the complex on the order of 10 Å or less.

To better determine the FRET efficiency between the Cy3 and Cy5 fluorophores within the ternary complex, and the potential efficiency of Cy3 "quenching," single-molecule experiments were performed where Cy3-labeled EF-Tu was surface immobilized within passivated, microfluidic reaction chambers via its N-terminal 6-His tag following previously published procedures (Zhao 2010). For these experiments the 6-His tag was not proteolytically removed after purification and labeling. Cy5-labeled Phe-tRNA$^{Phe}$ was then stopped-flow injected into the chamber and ternary complex formation was followed by the appearance of FRET (FIG. 5). The FRET value observed in the complex can be readily obtained from the raw data as the charged coupled device employed during imaging shows nearly identical sensitivities to both Cy3 and Cy5 fluorescence. The FRET efficiency of the interaction, determined by the ratio of Cy5 intensity over total intensity, is approximately 1 (the theoretical maximum), indicating a proximity between the Cy3 and Cy5 pair in the complex on the order of 10 Å. The Cy3 intensity drops to near zero in the complex and the complex is long-lived under the conditions of the experiment (ca. minutes). These experiments indicated that the sites of labeling on EF-Tu and tRNA were ideal for the proposed formation of a "quenched" ternary complex and that both the N-terminal 6-His and C-terminally fluorophore-labeled SFP tagged EF-Tu exhibited kinetic behaviors indistinguishable from those of the native EF-Tu protein.

Example 4

Comparison of Formation for Native and Quenched Ternary Complexes

To examine the detailed kinetics of ternary complex formation and the influence of the N- and C-terminal tagging strategies used in the "quenched" complex, time-resolved experiments were performed using a bulk stopped-flow instrument. The kinetics of ternary complex formation was followed using unlabeled forms of both native and genetically-modified EF-Tu.

Figure 6:
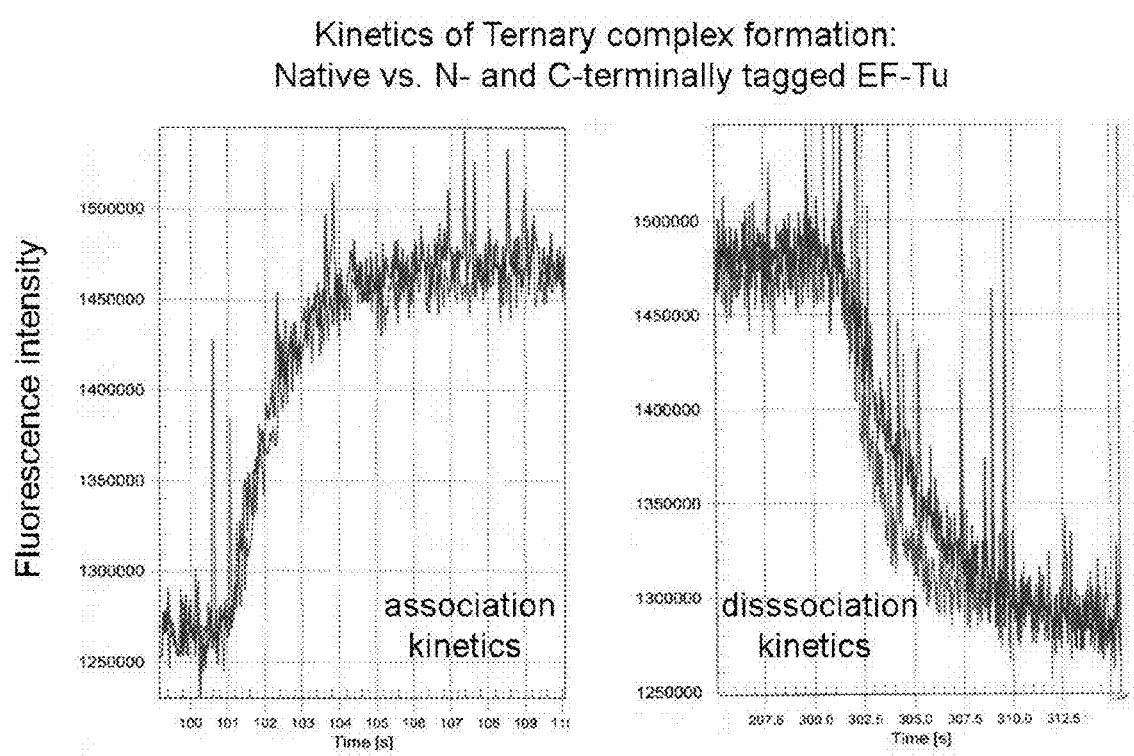
FIG. 6 illustrates the kinetics of ternary complex formation using native and genetically modified forms of EF-Tu. In the left panel, the kinetics of association between unlabeled native (red/dark) and N- and C-terminally tagged (green/light) EF-Tu followed by the increase in fluorescence intensity on Cy3-labeled Phe-tRNA$^{Phe}$. Experiments were performed by stopped-flow addition of saturating GTP concentrations to a solution of 5 nM Cy3-labeled Phe-tRNA$^{Phe}$ and 400 nM unlabeled EF-Tu. In the right panel, the kinetics of ternary complex dissociation for both native (red/dark) and N- and C-terminally tagged (green/light) EF-Tu were followed by a decrease in Cy3 fluorescence intensity caused by the irreversible dissociation of ternary complex upon stopped flow addition of saturating GDP (200 µM), a potent competitive inhibitor of ternary complex formation.

The kinetics of association between unlabeled native and N- and C-terminally tagged EF-Tu was followed by the increase in fluorescence intensity of Cy3-labeled Phe-tRNA$^{Phe}$ (FIG. 6). Experiments were performed by stopped-flow addition of saturating GTP concentrations to a solution of 5 nM Cy3-labeled Phe-tRNA$^{Phe}$ and 300 nM unlabeled EF-Tu. The kinetics of ternary complex dissociation for both native and native and N- and C-terminally tagged EF-Tu were followed by a decrease in Cy3 fluorescence intensity caused by the irreversible dissociation of ternary complex upon stopped flow addition of saturating GDP (200 µM), a potent competitive inhibitor of ternary complex formation. In these experiments, dye-labeling of EF-Tu with a "quencher" fluorophore species did not perturb the nature or kinetics of ternary complex formation.

Figure 3:
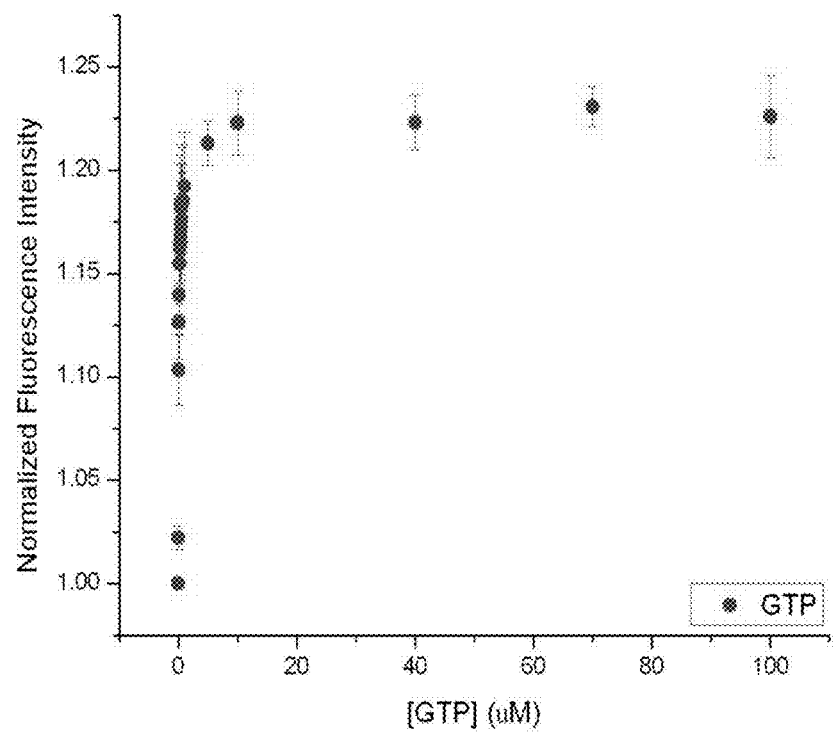
FIG. 3 illustrates the formation of ternary complex using components from *E. coli* followed by titrating GTP into a solution of Phe-tRNA$^{Phe}$ in the presence of saturating (300 nM) EF-Tu. Under these experimental conditions, fluorophore intensity increases as ternary complex is formed.
Figure 7:
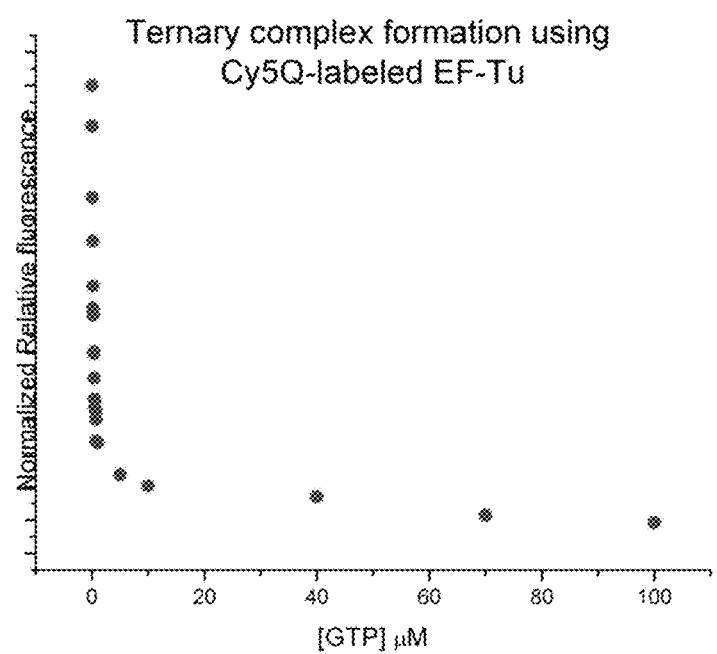
FIG. 7 shows that quencher-labeled EF-Tu has an affinity for Phe-tRNA$^{Phe}$ that is indistinguishable from the native EF-Tu protein.

An experiment identical to that shown in FIG. 3 was performed using EF-Tu-quencher with the quencher fluorophore Cy5Q. As seen in FIG. 7, a very clear decrease in Cy3 fluorescence intensity (linked to Phe-tRNA$^{Phe}$) is observed upon the addition of GTP consistent with efficient quenching of the fluorophore upon ternary complex formation. Notably, the apparent affinity of GTP for the complex is indistinguishable from that of native E. coli EF-Tu. These results strongly, as well as those shown in FIG. 6, are consistent with none of the modifications introduced into EF-Tu negatively affecting the kinetics of ternary complex formation. Thus, the "quenched" ternary complex is indistinguishable from that of the native system.

Example 5

EF-Tu Isolation and Labeling; Ternary Complex Purification

A. EF-Tu Isolation

A clone similar to the one described in Example 1 is grown and expressed in E. coli to produce EF-Tu with an N-terminal histidine tag and a C-terminal AcpS tag ("tagged EF-Tu"). To obtain the tagged EF-Tu, the cells are lysed, particulate material removed by centrifugation and the soluble fraction applied to a Ni or cobalt column.

After washing, the tagged EF-Tu is eluted from the column and stored for subsequent assays. EF-Ts is expressed and purified from laboratory strains of E. coli, such as DH5α, using affinity purification methods. Partially purified protein was further purified by FPLC using mono-Q and Sephadex-75 gel filtration resins.

A 1.2 molar excess of cleaved and FPLC-purified EF-Ts is incubated with 6-His tagged ACP-EF-Tu (or cleaved native EF-Tu) in the presence of 500 µm ATP, 100 µM GTP, 1 mM PEP, myokinase, pyruvate kinase at 37° C. for 30 minutes. The reaction is loaded onto a Sephadex 75 gel filtration column in Tu-Ts buffer (50 mM Tris pH 7.5, 100 mM NH4Cl, 50 mM KCl, 10 mM MgCl$_2$, 0.5 mM EDTA, 1 mM DTT) and Tu-Ts complex is purified as a single peak eluting at an apparent molecular weight of approximately 75 kilodaltons.

To attach the quencher, 100 µM Dye-CoA is incubated with 20 µM His$_6$-ACP-EF-Tu in complex with EF-Ts in the presence of 4 µM ACP-S enzyme in 50 mM Hepes pH 7.5, 10 mM MgCl$_2$ at 22° C. for 60 minutes (complex is labeled to approximately 100% within 10-30 minutes depending on the fluorophore used). The reaction is diluted two fold in nickel resing-binding buffer (50 mM Hepes pH 7.5, 50 mM NaCl, 10 mM Imidazole, 2 mM BME) and batch incubated with nickel-NTA resin rotating at 22° C. for 30 minutes. Next, resin is washed with the same buffer to separate free dye and the His$_6$-ACP-EF-Tu in complex with EF-Ts is eluted with nickel buffer containing 250 mM Imidazole. The elution pool is dialyzed against Tu-Ts buffer before the addition of 1/50th molar ratio of Tev protease and cleavage is allowed to proceed overnight at 4° C. Cleaved complex is collected as the flow through fraction passed over a second nickel-NTA column. This fraction is then concentrated and exchanged into Tu-Ts buffer in an Amicon-10K filter. Tu-Ts complex is reformed as above and injected over a Sephadex S75 column, collected and concentrated for storage and subsequent use for ternary complex formation. Using this protocol, achieves at least 80% or more labeling of EF-Tu without any significant loss of its activity.

B. Ternary Complex Formation

To maximize the utility of the "quenched" ternary complex for sequencing and/or mechanistic studies of translation using single-molecule methods (e.g., total internal reflection or zero mode waveguide (ZMW) methodologies), the "quenched" ternary complex is isolated as a pure entity using size-exclusion chromatography. Labeled tRNA is charged with amino acid in charging buffer (50 mM Tris-HCl pH 8, 20 mM KCl, 100 mM $NH_4Cl$, 1 mM DTT, 2.5 mM ATP, 0.5 mM EDTA, 10 mM $MgCl_2$) with the appropriate amino-acyl tRNA synthetase. Next, ternary complex is formed by adding an EF-Tu•EF-Ts complex to Phe-tRNA$^{Phe}$ (4:1) in T3 buffer (50 mM Hepes pH 7, 20 mM KCl, 100 mM $NH_4Cl$, 1 mM DTT, 2.5 mM ATP, 0.5 mM EDTA, 2.5 mM $MgCl_2$, 10 μM GTP) and incubated for 15 minutes at 37° C. The sample is purified using a Sephadex 75 gel filtration column on an Akta Purifier pre-equilibrated with T3 buffer. Ternary complex elutes at an apparent molecular weight of 75 kDa.

Figure 8:
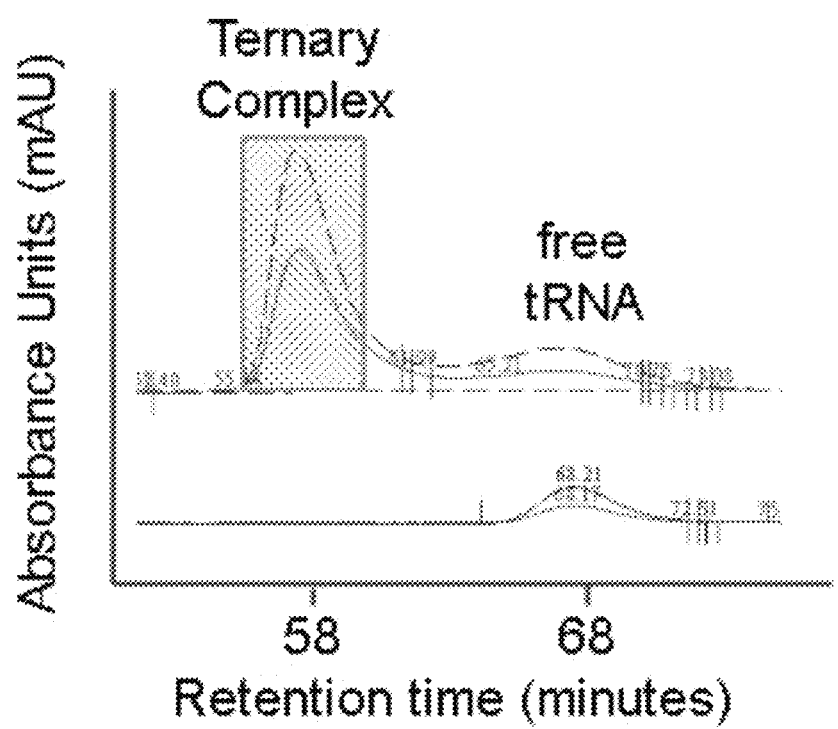
FIG. 8 is a plot showing the isolation of pure ternary complex by gel filtration chromatography using a Sephadex 75 column. Baseline resolution between ternary complex and free tRNA is achieved using this method.

FIG. 8 shows the separation achieved between ternary complex and free tRNA using unlabeled translation components. The kinetic data shown above, which show that the native and engineered forms of EF-Tu perform indistinguishably, indicates that analogous performance can be achieved using fully labeled components.

Example 6

Amino Acylation of tRNA Followed by Ternary Complex Formation

A. Formation by the Addition of Phenylalanine (Cy3-Quencher FRET)

Figure 9:
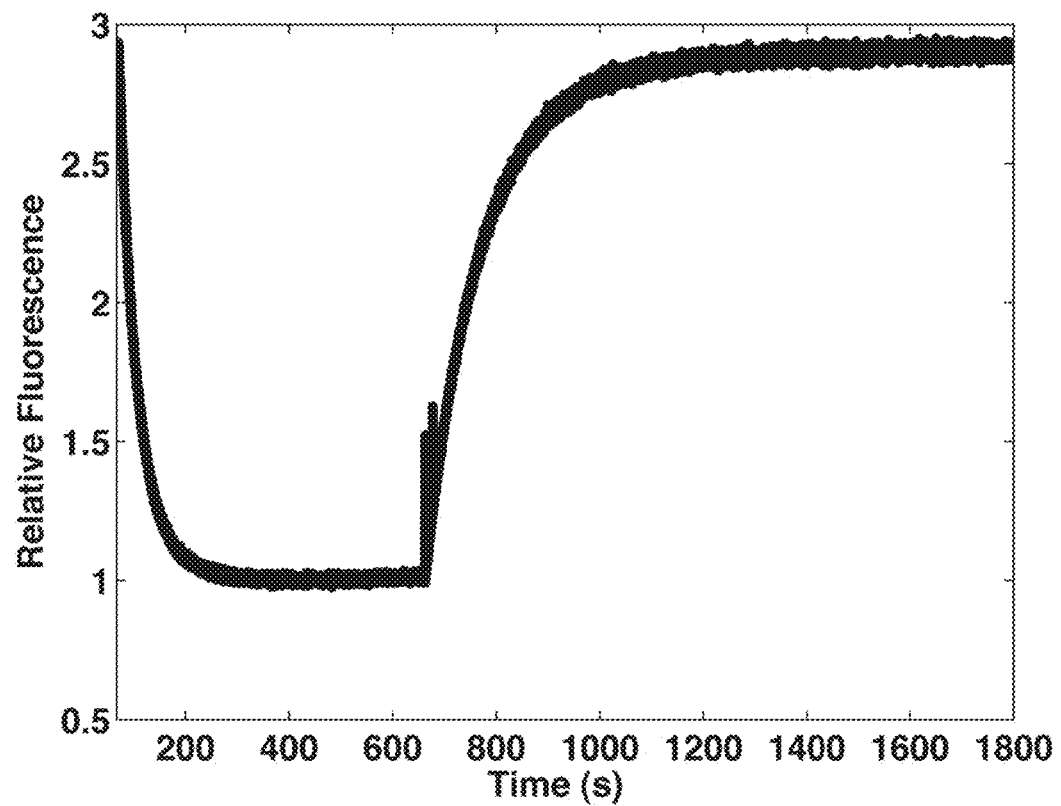
FIG. 9 illustrates the relative fluorescence for Cy3-quencher FRET in bulk solution of ternary complex formation upon the addition of phenylalanine which causes the aminoacylation of Cy3-labeled tRNA$^{Phe}$ by PheRS in the presence of Cy5(quencher)-EF-Tu. GDP addition dissociates the complex as observed for native complex.

Using stopped-flow methods, phenylalanine (50 μM) was stop-flow delivered to a solution of Cy3-tRNA (5 nM), PheRS (50 nM), and Cy5(quencher)-EF-Tu (400 nM) while exciting Cy3 at 532 nm and monitoring Cy3 emission intensity at 565 nm (FIG. 9). Relative fluorescence of Cy3 decreased 290% and was stable for more than 200 seconds. GDP (100 μM), which causes dissociation of the ternary complex was stop-flow delivered at 680 seconds and Cy3 intensity was observed to increase back to baseline.

B. Formation by the Addition of Phenylalanine (Cy3-Cy5 FRET)

Figure 10:
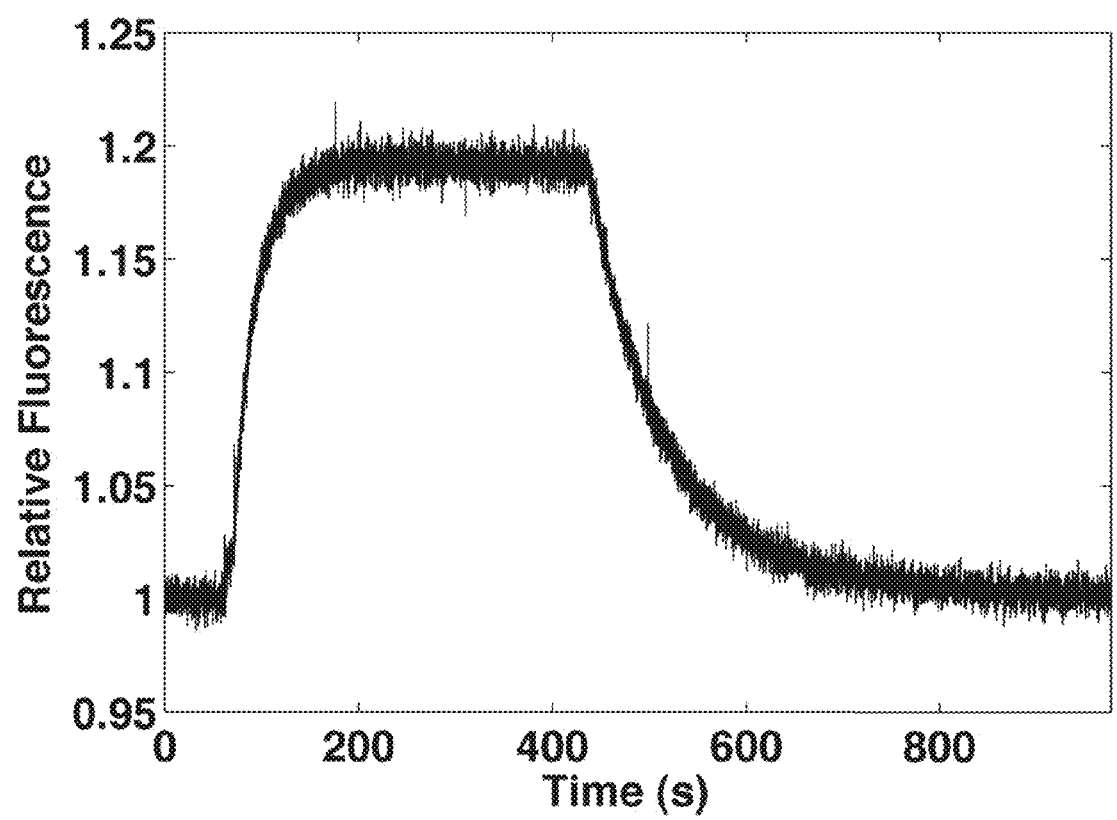
FIG. 10 illustrates the relative fluorescence for Cy3-Cy5 FRET in bulk measurements of ternary complex formation in response to the addition of phenylalanine which allows aminoacylation of Cy3-labeled tRNA$^{Phe}$ by PheRS and subsequent formation of ternary complex by Cy5-EF-Tu. GDP addition dissociates the complex as observed for native complex.

Using the same methods as above, phenylalanine (50 μM) was stop-flow delivered to Cy3-tRNA (5 nM), PheRS (50 nM), and Cy5-EF-Tu (400 nM) at 70 seconds while exciting Cy3 at 532 nm and monitoring Cy5 emission intensity at 665 nm (FIG. 10). Relative fluorescence of Cy5 increased 19.5% and was stable for more than 200 seconds. GDP (100 μM) was stop-flow delivered at 460 seconds and Cy5 intensity is observed to return back to baseline.

C. Binding of PheRS to Cy3-tRNA(Phe)

Figure 11:
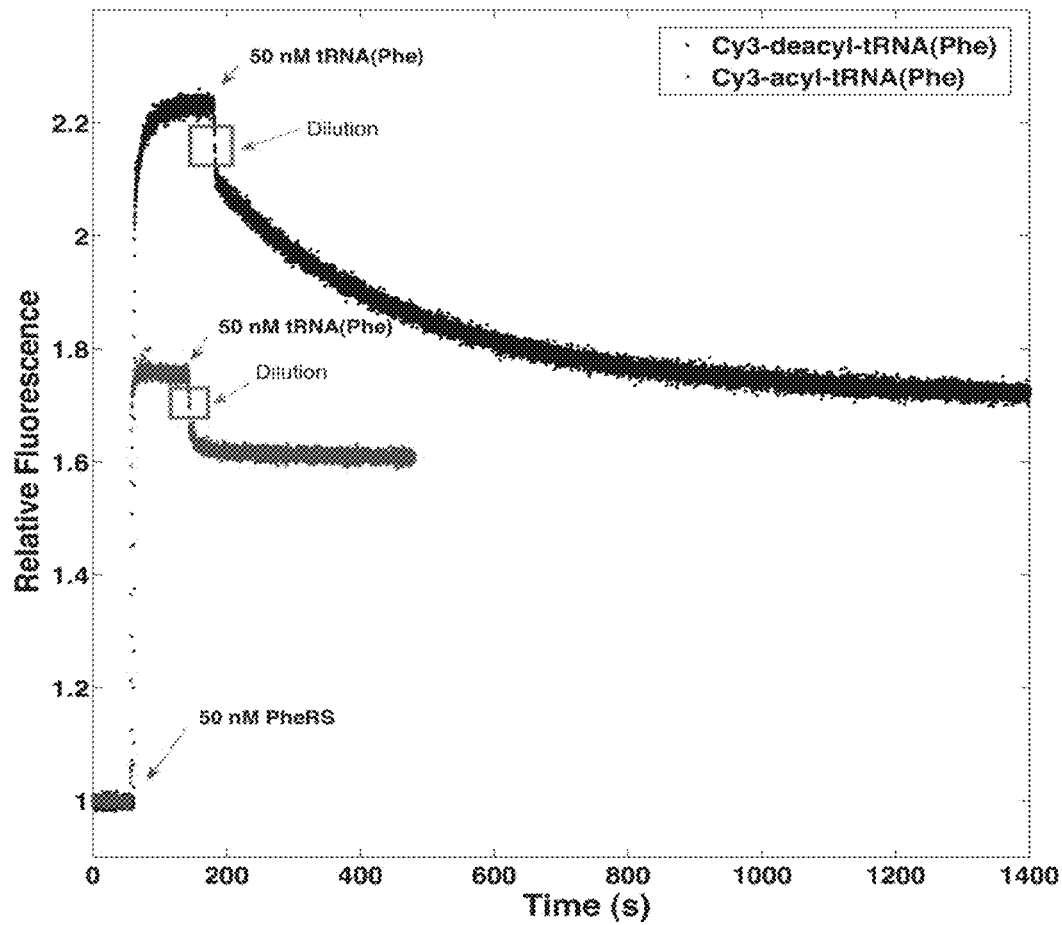
FIG. 11 illustrates changes in the relative fluorescence upon binding of PheRS to acylated and deacylated Cy3-labeled tRNA, followed by the addition of unlabeled, deacylated tRNA to compete out binding.

PheRS (50 nM) was added to 5 nM deacyl-tRNA$^{Phe}$ (black line) or 5 nM Phe-tRNA$^{Phe}$ (gray line). FIG. 11 shows the relative intensity of the Cy3 labeled tRNAs was monitored (excitation at 532 nm, emission at 565 nm). Unlabeled deacyl-tRNA$^{Phe}$ (50 nM) was then added to out-compete the labeled tRNA.

Example 7

Amino Acid Transport Assay

Figure 12:
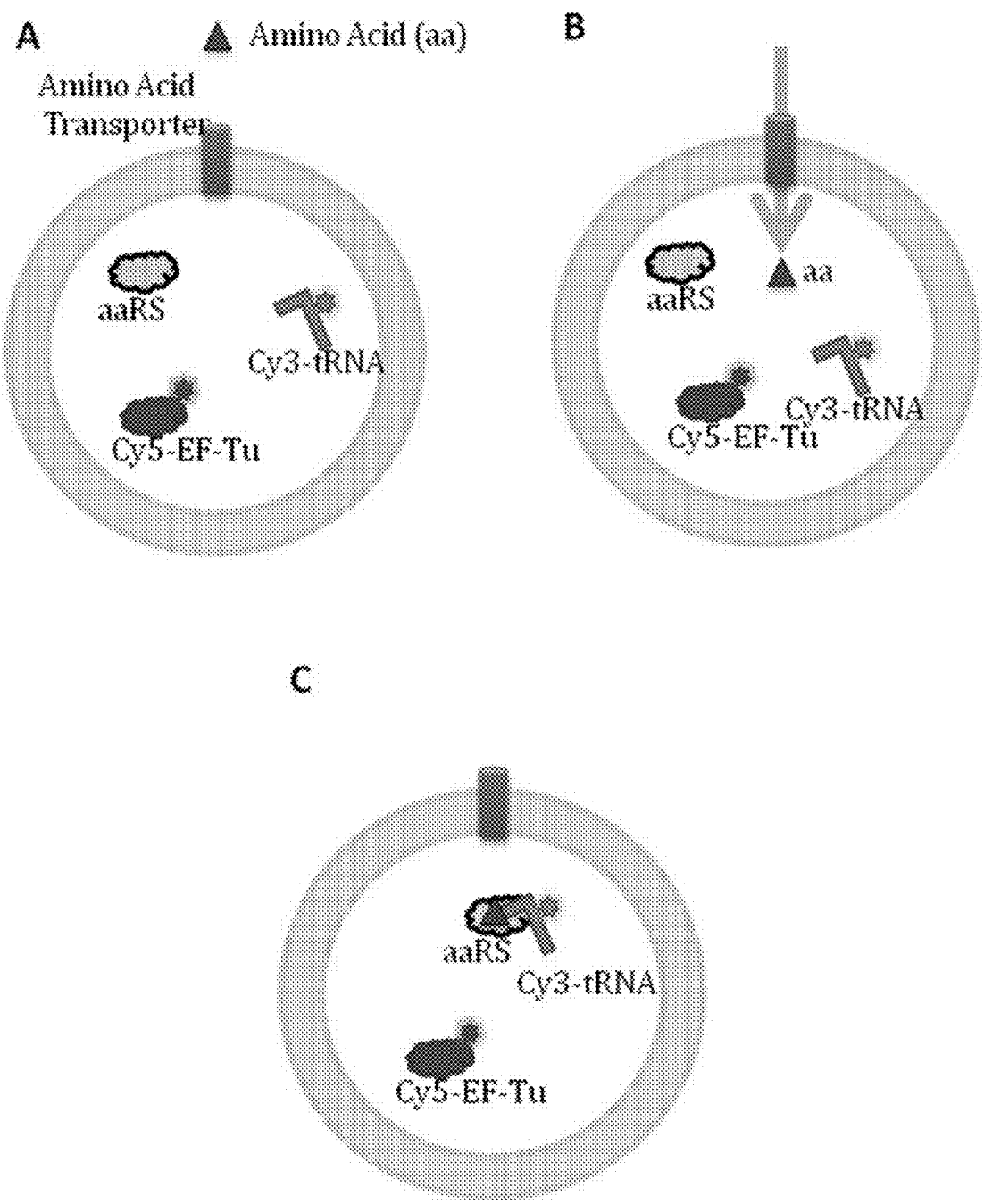
FIG. 12 illustrates the amino acid transport assay system. Panel A shows the encapsulation step in which dye-labeled tRNA along with dye-labeled EF-Tu and GTP is encapsulated into a lipid vesicle along with a aminoacyl-tRNA synthetase. In addition, small molecules such as ATP and GTP are encapsulated. Panel B shows the transport event in which the amino acid is transported by the amino acid transporter into the lipid vesicle. Panel C depicts the aminoacylation step which uses ATP available in the buffer, transported amino acid and the amino acid synthetase (aaRS) to acylate the encapsulated tRNA, resulting in the formation of ternary complex (aa-tRNA*EF-Tu(GTP)). The detection of ternary complex formation is achieved by changes in fluorescence of the dye-labeled aa-tRNA upon binding EF-Tu and FRET.

A schematic of the amino acid transport assay is shown in FIG. 12. This assay is based on the development of the FRET-based method for detecting the formation of the ternary complex of transfer-RNA (tRNA), elongation factor Tu (EF-Tu) and GTP in Example 6. Ternary complex (T3) formation depends on tRNA aminoacylation. In the assay tRNA aminoacylation is carried out by a tRNA synthetase (aaRS). T3 forms with nanomolar affinity and is stable enough to purify by size-exclusion chromatography when GTP is present.

Each of the components for the assay can be recombinantly expressed, purified to homogeneity and are fully active using in vitro translation and transport activity assays. T3 formation assays have been established using bulk fluorescence and FRET methods (Example 6). The findings from these preliminary studies suggest that the rates of T3 formation are ideally suited to sensing the individual LeuT transport events if even one molecule of each of the necessary components is present within the attoliter (ca. $10^{-18}$ L) lumen of 100-400 nm proteoliposomes (FIG. 12). At room temperature, LeuT transports at a rate of ~0.3 $min^{-1}$ and the estimated rate of T3 formation in the proteoliposomes lumen is ~24 $min^{-1}$. The components for T3 formation can be encapsulated within the proteoliposomes lumen simultaneous with the reconstitution of unlabeled LeuT molecules into the lipid bilayer. Here, we can use native tRNA$^{Phe}$ or tRNA$^{Ala}$ molecules, site-specifically labeled with the donor fluorophore Cy3 at naturally occurring modified nucleotides ($acp^3U47$ and $s^4U8$, respectively) and EF-Tu-quencher. The components of T3 are encapsulated into the proteoliposomes lumen by bathing pre-formed LeuT proteoliposomes with T3 formation buffer containing equimolar concentrations of Cy3-labeled, deacylated tRNA, Cy5-labeled EF-Tu, aaRS and GTP and subjecting the solution to a single freeze thaw followed by extrusion through a 400 nm polycarbonate filter mechanism. The liposomes also include biotinylated lipids for surface immobilization. The liposomes are adhered to a slide for total internal reflectance microscopy, amino acid added and imaged using smFRET techniques to evaluate transport.

Example 8

Visualization of Active HIF-1α Translation in Living Cells

Quenched forms of ternary complex are used to investigate spatio-temporal aspects of specific mRNA translation in living cells, and are particularly useful for mRNAs associated with specific cellular bodies. One such example is found with the hypoxia inducible factor 1α (HIF-1α), which encodes a master transcriptional regulator, and for which microtubules play an active role in orchestrating the translation of HIF-1α, as microtubule-dependent trafficking of HIF-1α mRNA is required for its efficient translation. Hence, when microtubules are disrupted, either by stabilization or depolymerization, the transport of HIF-1α mRNA is halted, and HIF-1α is instead recruited into P-bodies. This change in localization is accompanied by the release of HIF-1α mRNA from actively translating polysomes.

To examine this process, fluorescently-labeled aminoacylated tRNA substrates and quencher-labeled EF-Tu in a ternary complex are microinjected into a cell and used for identifying actively translating ribosomes on microtubules by directly imaging the process of protein synthesis in living cells. Fluorescence is detected by the smFRET imaging techniques described herein. Such experiments are done in the presence and absence of microtubule disrupters. Following injection of such ternary complexes into living cells very little background fluorescence is observed, whereas active sites of translation are marked by the appearance of localized bursts of fluorescence above the cellular autofluorescence each time the fluorescently labeled aa-tRNA incorporates into the ribosome. Localization of the HIF1α mRNA can also be followed my microinjection of a HIF1α molecular beacon.

To detect signals that are specific for active sites of HIF1α translation, this technique is extended by measuring FRET between sequentially incorporated fluorescently labeled tRNA molecules into engineered HIF1α transcripts that are simultaneously microinjected along with ternary complex. Such transcripts contain template sequences that encode site-specifically introduced heteropolymeric stretches and result in the incorporation of the specific ternary complexes.

Such strategies, with the simultaneous expression of fluorescent tubulin constructs that mark the microtubule network present in the cell, identify active sites of HIF1α translation and their association with microtubule filaments.

Example 9

Ternary Complex Drug Screening Assay

A. Methods

EF-Tu and EF-Ts Preparation:
Both EF-Tu and EF-Ts were purified by Ni-NTA affinity chromatography as previously described (Blanchard 2004a).
Purification and Labeling of *E. coli* tRNA$^{Phe}$:
Native *E. Coli* tRNA$^{Phe}$ was purified and labeled with cyanine 3 at position U47 as previously described (Dunkle et al 2011, Munro 2007). Purified tRNA$^{Phe}$ was aminoacylated by mixing 7.5 picomoles of labeled tRNA with 6 picomoles phenylalanyl-tRNA synthetase and 10 nanomoles of phenylalanine amino acid in a volume of 10 μL in buffer A (50 mM Tris-HCl pH 8, 20 mM KCl, 100 mM NH$_4$Cl, 1 mM DTT, 2.5 mM ATP, 0.5 mM EDTA, 10 mM MgCl$_2$). The sample was then incubated at 37° C. for 10 minutes.

EF-Tu/EF-Ts Complex Formation:
Purified EF-Tu is added with EF-Ts (1:1.1) into buffer B (50 mM Tris-HCl pH 7.5, 100 mM NH$_4$Cl, 10 mM MgCl$_2$, 0.5 mM EDTA, 50 mM KCl) to a final volume of 1 mL. The sample was then incubated in a water bath at 37° C. for 20 minutes. EF-Tu/EF-Ts binary complexes are isolated by Sephadex 75 gel filtration chromatography, pre-equilibrated in buffer A. The complex is then stored in buffer C (10 mM Tris-Acetate pH 7, 50 mM KCl, 1 mM DTT, 50% Glycerol) at −20° C.

Fluorescence Measurements and Equilibrium Titration of Experiments:
Fluorescence experiments were performed using a Photon Technology International fluorescence meter with a 550 nm high pass filter on the emission side. All samples were analyzed in a 3 mL quartz cuvette, with a stir bar, maintained at 23° C. The equilibrium constants of ternary complex formation were measured by titrating either EF-Tu•EF-Ts or nucleotide into 5 nM Cy3 labeled Phe-tRNA$^{Phe}$ in buffer D (50 mM Hepes pH 7, 20 mM KCl, 100 mM NH$_4$Cl, 1 mM DTT, 2.5 mM ATP, 0.5 mM EDTA, 2.5 mM MgCl$_2$, 10 μM GTP) or buffer E (50 mM Hepes pH 7, 20 mM KCl, 100 mM NH$_4$Cl, 1 mM DTT, 2.5 mM ATP, 0.5 mM EDTA, 2.5 mM MgCl$_2$, 400 nM EF-Tu/EF-Ts). Fluorescence intensity was measured by exciting Cy3 labeled tRNA$^{Phe}$ with 532 nm light and recording emission intensities at 565 nm. The sample was allowed to mix for 1 minute after each subsequent addition of reagent before data acquisition.

Equilibrium Parameter Determination:
Assuming negligible tRNA deacylation the total observed fluorescence emission intensity may be expressed as:

$$F = C_f E_f + C_b E_b \tag{4}$$

(Abrahamson 1985), where $E_f$ and $E_b$ represent the emission intensity of aa-tRNA$^{aa}$ in the free, unbound state and the bound state respectively and $C_f$ and $C_b$ are the concentrations of tRNA$^{aa}$ in the free state and the bound state respectively. The relative fluorescence as a function of EF-Tu concentration is given by:

$$\frac{F}{F_0}(T) = 1 + \frac{\left[\left(\frac{F}{F_0}\right)_{max} - 1\right]}{2C_0}\left[C_t + T + K_d - \sqrt{(C_t + T + K_d)^2 - 4C_t T}\right] \tag{5}$$

(Abrahamson 1985). Values of $K_d$ were obtained by performing a nonlinear least squares fit of the data from fluorescence experiments to equation 5 in Matlab (R2011a). The best-fit values are reported with asymptotic 95% confidence intervals.

Ternary Complex Formation Kinetics:
With the equilibrium experiments as a basis, an assay was developed to follow the increase in fluorescence magnitude corresponding to ternary complex formation in real time. Fluorescent measurements were performed at 10 readings per second upon addition of 7.5 pmoles of EF-Tu•EF-Ts into 5 nM Phe-tRNA$^{Phe}$ in buffer D. The time dependent experiment was analyzed by assuming the molecular reaction given in equation 3 which is governed by the relative rates of ternary complex formation and dissociation. In terms of fluorescence, the rate of ternary complex formation is given by the rate of relative fluorescence change with respect to time, dictated by the following equation:

$$\frac{d}{dt}RF(t) = RF_{max}[Tu]k_+ - RF(t)([Tu]k_+ + k_-) \tag{6}$$

where RF is the relative fluorescence as a function of time, [Tu] is the concentration of EF-Tu added to the reaction chamber, and are the respective on and off rates for ternary complex given in eq 3. Upon integration, equation 6 equates to:

$$RF(t) = C_1 + C_2 e^{C_1 t} \tag{7}$$

where $$C_1 = \frac{RF_{max}[Tu]K_+}{[Tu]k_+ + k_-}$$

$$C_2 = -\frac{1}{[Tu]k_+ + k_-}$$

$$C_3 = -([Tu]k_+ + k_-)$$

Time-based data of ternary complex formation, taken in triplicate, is used to generate a fit based on eq 7.

Ternary Complex Isolation by Gel Filtration Chromatography:

Ternary complex was formed by adding previously formed EF-Tu•EF-Ts complex to Phe-tRNA$^{Phe}$ (4:1) in buffer D and incubated for 15 minutes in a 37° waterbath. The sample was purified using a Sephadex 75 gel filtration column on an Akta Purifier pre-equilibrated with buffer D either with or without GTP. Samples eluted at an apparent molecular weight of 75 kDa (FIG. 3).

Antibiotic Preparation:

Kirromycin and Thiostrepton were purchased from Sigma and also resuspended in 100% DMSO to 1 mM. All antibiotics were stored at −80° C. until further use.

Drug Assay:

Ternary complex was formed by the addition of 400 nM EF-Tu•EF-Ts to 5 nM of Cy3-labeled Phe-tRNA$^{Phe}$ in buffer D using the same fluorometer settings as described above. After ternary complex was formed, drug was added to a final concentration of 1 µM. Decay curves were fit using non-linear least squares method as previously mentioned.

B. Results

Figure 13:
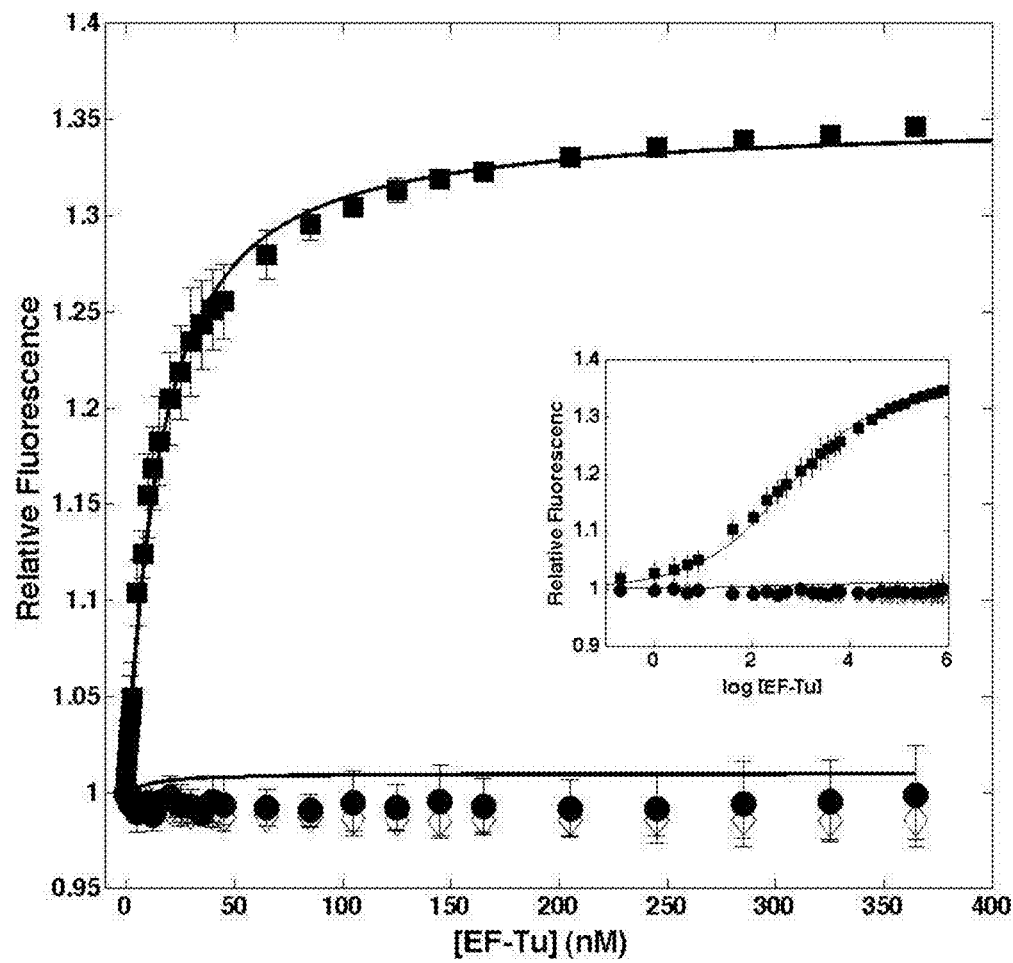
FIG. 13 demonstrates an experiment for measuring EF-Tu affinity for aa-tRNA. The affinity of EF-Tu for aa-tRNA was determined by titrating EF-Tu into a solution of fluorophore labeled Phe-tRNA either acylated (squares) or deacylated (circles). As a control, this was repeated without GTP (open diamonds). Error bars represent 95% CI of 3 separate experiments.

The ternary complex formation assays measured the change in relative fluorescence intensity upon EF-Tu binding of the Cy3 fluorophore linked to the naturally occurring modified nucleotide, acp$_3$U, at position 47 of tRNA$^{Phe}$. Under the present experimental conditions, ternary complex formation results in an approximately 30% increase in fluorescence intensity of the Cy3 fluorophore (FIG. 13). Such changes likely arise from alterations in Cy3 quantum yield that report on subtle changes in tRNA conformation and/or environment.

Ternary Complex Formation is Strictly Dependent on GTP and the Aminoacyl Moiety of tRNA.

To determine the apparent affinity of EF-Tu for Phe-tRNA$^{Phe}$, titration experiments were performed at room temperature (23° C.) with increasing concentrations of EF-Tu manually added to a solution containing 5 nM Phe-tRNA$^{Phe}$ (Cy3-acp$_3$U47) in the presence of 10 µM GTP. Under the current experimental conditions, the formation of EF-Tu•GTP is not rate limiting. (Gromadski 2002). By taking advantage of the intrinsic guanine nucleotide exchange activity of EF-Ts, a homogeneous population of EF-Tu•GTP was maintained and avoided previously reported problems of subpopulations of EF-Tu being inactive (Cai 2000; Louie 1985). The increase in Cy3 fluorescence intensity was found to be strictly dependent on the presence of GTP and the aminoacyl moiety (FIG. 13). These data, fit to equation 5, revealed an apparent dissociation constant between EF-Tu•GTP and Phe-tRNA$^{Phe}$ of 12.6 nM with a 95% CI of ±1.1 nM. This is in agreement with previous measurements where ternary complex formation was monitored by changes in fluorophore intensity linked to position s$_4$U8.

Ternary Complex is Intrinsically Unstable when GTP is in Dynamic Exchange.

Figure 14:
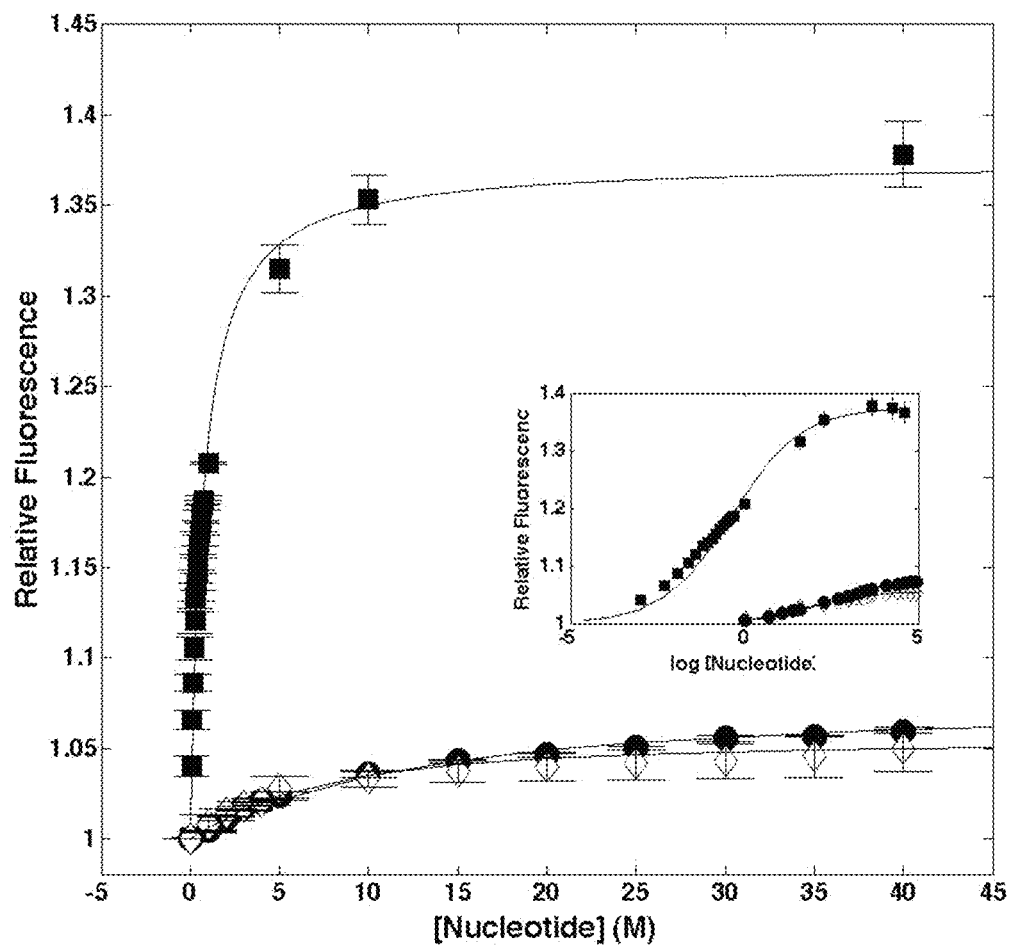
FIG. 14 shows that GTP affinity for ternary complex is greater than non-hydrolysable GTP analogs. GTP (squares), GDPNP (circles), or GDPyS (open diamonds) is titrated into a cuvette containing fluorophore-labeled tRNA and EF-Tu. Error bars represent 95% CI of 3 separate experiments.

To assess the affinity and nature of GTP's interactions with ternary complex, analogous titration experiments were carried out in which GTP was added to a solution of 5 nM Phe-tRNA$^{Phe}$ (Cy3-acp$_3$U47) in the presence of saturating concentrations of EF-Tu (40 times IQ). Here, an analogous increase in Cy3 fluorescence intensity was observed in a GTP concentration dependent manner (FIG. 14). Fitting the data to the equation above revealed that the apparent affinity of GTP for the complex was 696 nM with a 95% CI of ±5 nM (Table 1). These experiments were repeated with the non-hydrolysable GTP analogs guanylyl-imino-diphosphate (GDPNP) and guanosine 5'[γ-thio]triphosphate (GDPγS) to ascertain if they also exhibited a distinct K$_d$ for ternary complex. The K$_d$ of GDPNP and GTPγS were each observed to be an order of magnitude greater than GTP and did not elicit the same relative fluorescence increase after plateauing upon saturation (FIG. 14; Table 1). The non-hydrolysable analogs each saturated at a relative fluorescence value well below 30%, illustrating EF-Tu's sensitivity to the position of the gamma phosphate.

TABLE 1

Affinity of EF-Tu and nucleotides to ternary complex.

| Substrate | Kd (nM) | RF Increase (%) |
|---|---|---|
| EF-Tu (GTP) | 12.66 ± 1.1 | 30 |
| GTP | 696 | 30 |
| GDPNP | 9270 | 7.3 |
| GDPγS | 3671 | 5.5 |

Figure 15:
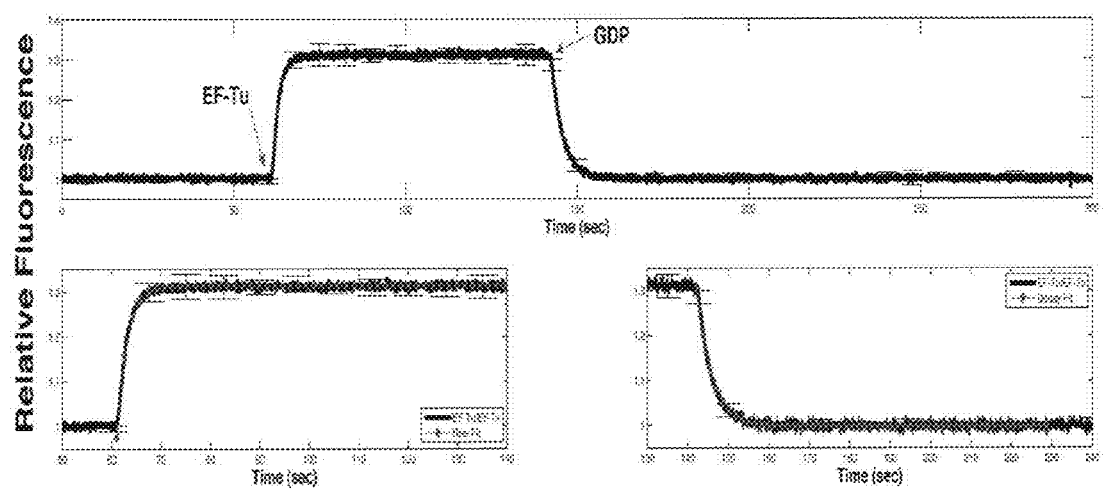
FIG. 15 illustrates ternary complex formation by stop-flow delivery of EF-Tu. Top panel, EF-Tu complexed with EF-Ts is stop-flow delivered to fluorophore-labeled Phe-tRNAPhe (60 seconds) resulting in a 30% rise in fluorescence intensity. GDP is then stop-flow delivered (145 seconds) and returning fluorescence to its initial intensity. Bottom panels, apparent rates of ternary complex formation (kapp,1) and decay (kapp,2) are obtained by fitting to single exponential. Error bars represent 95% CI of 3 separate experiments.

These data suggest that the nature of GTP's interactions with ternary complex is distinct from those of its other components. One explanation for this finding is that GTP may have distinct rate constants from the complex. To test this hypothesis, ternary complex was formed at low, saturating concentrations of GTP (10 µM). As expected, a fluorescence intensity increase of 30% was observed (FIG. 15). To the formed complex, 100 µM GDP was then added and the rate of ternary complex dissociation was followed as a function of time. These data revealed that ternary complex rapidly breaks down in the presence of GDP at a rate of 0.3 s$^{-1}$.

These data are consistent with a model in which ternary complex remains in dynamic exchange at saturating concentrations of EF-Tu and GTP, where GDP can exchange for GTP on EF-Tu. Given that the apparent K$_d$ of EF-Tu and GTP for ternary complex are distinct (compare FIGS. 13 and 14), these data suggest that GTP dynamically exchanges on and off of the binary complex of EF-Tu•Phe-tRNA$^{Phe}$ and that the binary complex decays at the observed rate of 0.3 s$^{-1}$, followed by effectively irreversible GDP binding (affinity for GDP is 40 fold greater than GTP). In this model, the k$_{on}$ of GTP for the complex (k$_{on}$=k$_{off}$/K$_D$) is substantially slower than a diffusion limited process, on the order of 1×10$^6$ M$^{-1}$ s$^{-1}$.

Direct Measurements of the Kinetics of Ternary Complex Formation.

To specifically examine the kinetic features of ternary complex formation, time-lapse measurements were performed. The kinetics of association were followed upon the stopped-flow addition of EF-Tu and GTP (10 µM) to a solution of 5 nM Cy3-labeled Phe-tRNA$^{Phe}$ (FIG. 15). As described above, the kinetics of ternary complex dissociation were followed by stopped-flow addition of GDP at saturating concentrations. Fitting the triplicate time course of relative fluorescence intensities to equation 7 produced an association constant k$_{on}$ of 1.4 µM$^{-1}$ s$^{-1}$ and a dissociation rate k$_{off}$ of 0.08 s$^{-1}$. This is consistent with the rate of association of 1.5 µM$^{-1}$ s$^{-1}$ determined previously at 4° C., pH 7.4.

Figure 16:
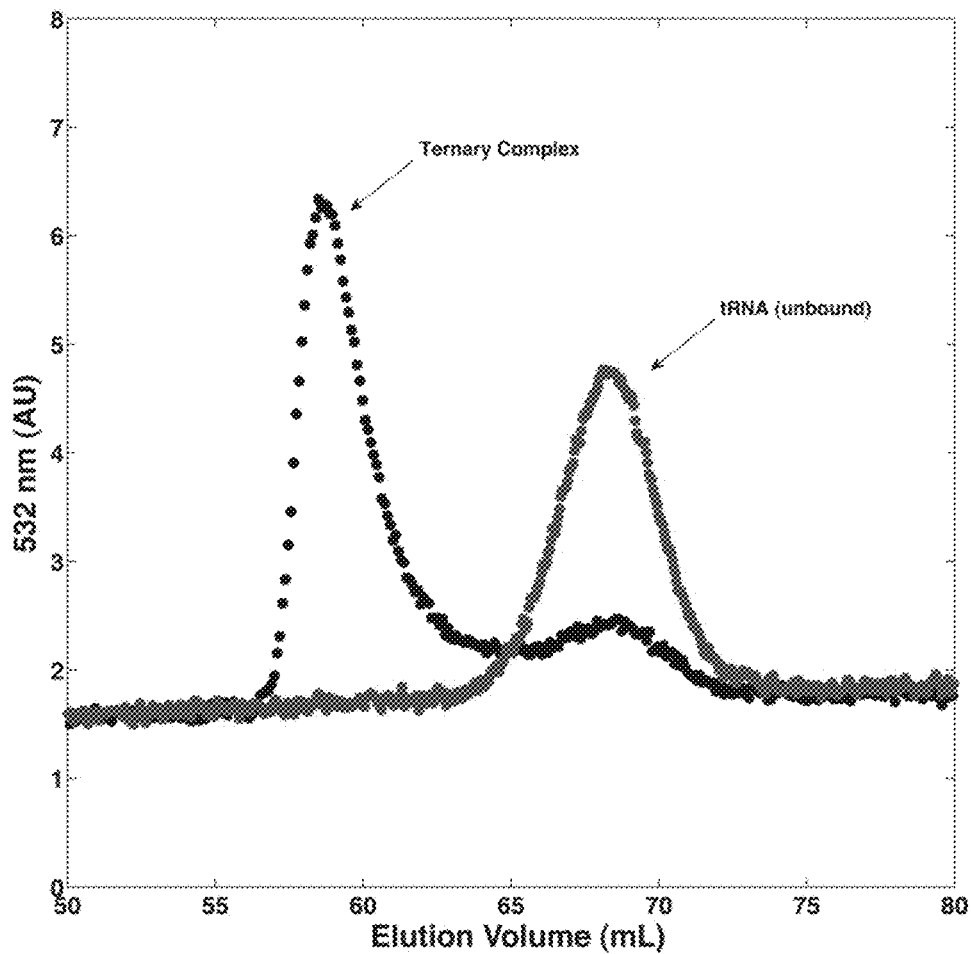
FIG. 16 shows the isolation of ternary complex by gel filtration chromatography. Ternary complex was formed as described in Example 9 and injected over a 120 mL volume S75 gel filtration column equilibrated in buffer with (black) or without (red) GTP. Cy3 absorbance monitored to elucidate the tRNA containing fractions.

Isolation of Ternary Complex:

Based on these results, the stability of ternary complex was examined by gel filtration chromatography. The proposed model predicted that ternary complex, when efficiently separated from GTP during flow, would rapidly dissociate making the isolation of ternary complex impossible. Indeed, as shown in FIG. 16, the chromatographic isolation of ternary complex revealed that only a small fraction of Phe-tRNA$^{Phe}$, <5%, participated in ternary complex in the absence of nucleotide in the column buffer. However, when experiments were repeated with 10 μM GTP in solution, ternary complex could be efficiently isolated, eluting at an apparent molecular weight of ~75,000 Da.

A Functional Assay for the Investigation of Drugs:

To illustrate the dynamic equilibrium that exists between ternary complex and its constituents, EF-Tu-targeting drugs were delivered to pre-formed ternary complex in the same manner as GDP described above. Ternary complex was formed by the addition of 400 nM EF-Tu/EF-Ts to a solution containing 5 nM Cy3 labeled aa-tRNA$^{aa}$ in the presence of 10 μM GTP.

Figure 17:
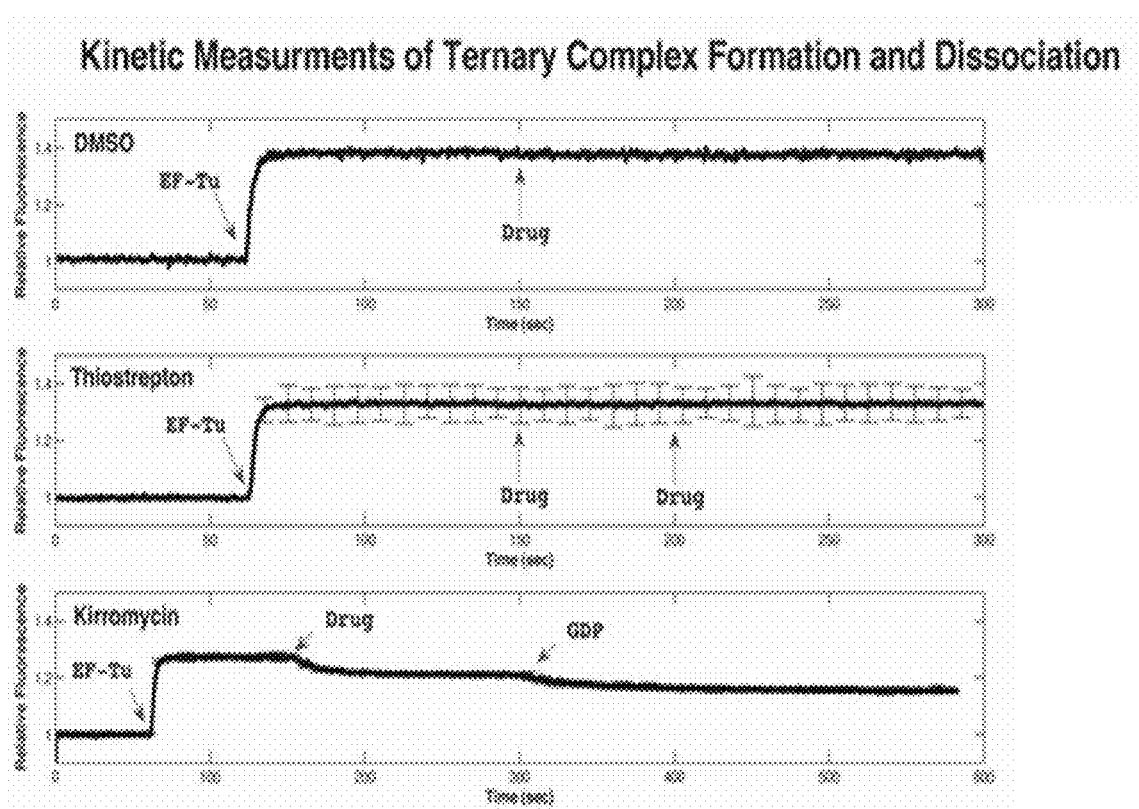
FIG. 17 depicts the relative fluorescence in a functional assay for the comparison of factor targeting antibiotics. Ternary complex is formed by the addition of 400 nM EF-Tu/EF-Ts (at 60 seconds) followed by the addition of 1 µM drug (at 150 seconds) and 10 µM thiostrepton (at 200 seconds) (middle panel) or 1 µM kirromycin drug (at 150 seconds) followed by GDP (bottom panel).

Once ternary complex was formed and observed to be stable, drugs were added and fluorescence was monitored. Addition of a ternary complex disruptor leads to a marked decrease in fluorescence. The addition of thiostrepton, a known target of the E. coli large ribosomal subunit and not recognized to bind to EF-Tu did not lead to disruption of the ternary complex (FIG. 17, middle panel). The addition of 1 μM kirromycin, an EF-Tu targeting antibiotic shown to stall protein synthesis after EF-Tu mediated GTP hydrolysis, reduced the relative fluorescence by ~20% indicating a new dynamic equilibrium or a subtle change to the conformation of either EF-Tu or aa-tRNA (FIG. 17, bottom panel). However, with kirromycin present, the addition of saturating GDP did not dissociate ternary complex in the time frame observed, suggesting a resistance to GTP release from EF-Tu, consistent with known effects of kirromycin bound ternary complex on the ribosome (Table 2).

TABLE 2

Apparent rates of ternary complex dissociation.

| Compound | $k_{app,2}$ (s$^{-1}$) |
|---|---|
| GDP | 0.30 |
| Thiostrepton | 0 |
| Kirromycin | 0.02* |

*Rate of GDP mediated dissociation in the presence of 1 μM kirromycin.

REFERENCES

Abrahamson, J. K., Laue, T. M., Miller, D. L. & Johnson, A. E. Direct determination of the association constant between elongation factor Tu. GTP and aminoacyl-tRNA using fluorescence. Biochemistry 24, 692-700 (1985).

Aitken, C. E., Marshall, R. A. & Puglisi, J. An oxygen scavenging system for improvement of dye stability in single-molecule fluorescence experiments. Biophys. J., biophysj.107.117689 (2007).

Blanchard et al. (2010). Methods and compositions for altering photophysical properties of fluorophores via proximal quenching. Intl. Publication No. WO2010/096720.

Blanchard, S. C., Gonzalez, R. L., Kim, H. D., Chu, S. & Puglisi, J. D. (2004b). tRNA selection and kinetic proofreading in translation. Nat Struct Mol Biol 11, 1008-14.

Blanchard, S. C., Kim, H. D., Gonzalez, R. L., Jr., Puglisi, J. D. & Chu, S. (2004a). tRNA dynamics on the ribosome during translation. Proc Natl Acad Sci USA 101, 12893-8.

Dave, R., Terry, D. S., Munro, J. B. & Blanchard, S. C. Mitigating Unwanted Photophysical Processes for Improved Single-Molecule Fluorescence Imaging. Biophys J 96, 2371-2381 (2009).

Dorner, S., Brunelle, J. L., Sharma, D. & Green, R. The hybrid state of tRNA binding is an authentic translation elongation intermediate. Nat Struct Mol Biol 13, 234-241 (2006).

Gromadski, K. B., Daviter, T. & Rodnina, M. V. (2006). A uniform response to mismatches in codon-anticodon complexes ensures ribosomal fidelity. Mol Cell 21, 369-77.

Johansson, M., Lovmar, M. & Ehrenberg, M. (2008). Rate and accuracy of bacterial protein synthesis revisited. Curr Opin Microbiol 11, 141-7.

Kim, H. D., Puglisi, J. D. & Chu, S. (2007). Fluctuations of Transfer RNAs between Classical and Hybrid States. Biophys J 93, 3575-3582.

Lee, T.-H., Blanchard, S. C., Kim, H. D., Puglisi, J. D. & Chu, S. (2007). The role of fluctuations in tRNA selection by the ribosome. Proceedings of the National Academy of Sciences 104, 1366113665.

Louie, A. and Jurnak, F. (1985). "Kinetic Studies of Escherichia coli Elongation Factor Tu-Guanosine 5'-Triphosphate-Aminoacyl-tRNA Complexes." Biochemistry 24: 6433-6439.

Lovmar, M. & Ehrenberg, M. (2006). Rate, accuracy and cost of ribosomes in bacterial cells. Biochimie 88, 951-61.

Munro, J. B. et al. Spontaneous formation of the unlocked state of the ribosome is a multistep process. Proc Natl Acad Sci USA 107, 709-14 (2010a).

Munro, J. B., Altman, R. B., O'Connor, N. & Blanchard, S. C. Identification of two distinct hybrid state intermediates on the ribosome. Mol Cell 25, 505-17 (2007).

Munro, J. B., Sanbonmatsu, K. Y., Spahn, C. M. & Blanchard, S. C. Navigating the ribosome's metastable energy landscape. Trends Biochem Sci 34, 390-400 (2009).

Ninio, J. (2006). Multiple stages in codon-anticodon recognition:double-trigger mechanisms and geometric constraints. Biochimie 88, 963-992.

Nirenberg, M. & Leder, P. (1964). Rna Codewords and Protein Synthesis. The Effect of Trinucleotides Upon the Binding of Srna to Ribosomes. Science 145, 1399-407.

Ogle, J. M., Carter, A. P. & Ramakrishnan, V. (2003). Insights into the decoding mechanism from recent ribosome structures. Trends Biochem Sci 28, 259-66.

Pan, D., Kirillov, S. & Cooperman, B. S. Kinetically competent intermediates in the translocation step of protein synthesis. Mol Cell 25, 519-529 (2007).

Parker, J. (1989). Errors and alternatives in reading the universal genetic code. Microbiol. Rev 53, 273-298.

Parmeggiani, A., I. M. Krab, et al. (2006). "Structural basis of the action of pulvomycin and GE2270 A on elongation factor Tu." Biochemistry 45(22): 6846-57.

Parmeggiani, A., I. M. Krab, et al. (2006). "Enacyloxin IIa pinpoints a binding pocket of elongation factor Tu for development of novel antibiotics." J Biol Chem 281(5): 2893-900.

Perla-Kajan, J., Lin, X., Cooperman, B. S., Goldman, E., Jakubowski, H., Knudsen, C. R. & Mandeki, W. Properties of Escherichia coli EF-Tu mutants designed for fluorescence resonance energy transfer from tRNA molecules. Protein Eng. Des. Sel. 23, 129-136 (2010).

Peske, F., Savelsbergh, A., Katunin, V. I., Rodnina, M. V. & Wintermeyer, W. Conformational changes of the small ribosomal subunit during elongation factor G-dependent tRNA-mRNA translocation. J Mol Biol 343, 1183-94 (2004).

Petrov, A., G. Kornberg, et al. (2011). "Dynamics of the translational machinery." *Curr Opin Struct Biol* 21(1): 137-45.

Qin, F. Restoration of single-channel currents using the segmental k-means method based on hidden Markov modeling. Biophys J 86, 1488-501 (2004).

Qin, F., Auerbach, A. & Sachs, F. Estimating single-channel kinetic parameters from idealized patch-clamp data containing missed events. Biophys J 70, 264-280 (1996).

Ramakrishnan, V. (2002). Ribosome structure and the mechanism of translation. *Cell* 108, 557-72.

Rodnina, M. V. (2009). Long-range signalling in activation of the translational GTPase EF-Tu. *Embo J* 28, 619-20.

Rodnina, M. V., Gromadski, K. B., Kothe, U. & Wieden, H. J. (2005). Recognition and selection of tRNA in translation. *FEBS Lett* 579, 938-42.

Rush, J. S.; Bertozzi, C. R. New Aldehyde Tag Sequences Identified by Screening Formylglycine Generating Enzymes in Vitro and in Vivo. J. Am. Chem. Soc. 2008, 130, 12240-12241.

Schmeing, T. M. & Ramakrishnan, V. (2009). What recent ribosome structures have revealed about the mechanism of translation. *Nature* 461, 1234-42.

Schmeing, T. M., Voorhees, R. M., Kelley, A. C., Gao, Y. G., Murphy, F. V. t., Weir, J. R. & Ramakrishnan, V. (2009). The crystal structure of the ribosome bound to EF-Tu and aminoacyltRNA. *Science* 326, 688-94.

Schuette, J. C., Murphy, F. V. t., Kelley, A. C., Weir, J. R., Giesebrecht, J., Connell, S. R., Loerke, J., Mielke, T., Zhang, W., Penczek, P. A., Ramakrishnan, V. & Spahn, C. M. (2009). GTPase activation of elongation factor EF-Tu by the ribosome during decoding. *EMBO J.*

Semenkov, Y. P., Rodnina, M. V. & Wintermeyer, W. (2000). Energetic contribution of tRNA hybrid state formation to translocation catalysis on the ribosome. *Nat Struct Biol* 7, 1027-31.

Sherlin, L. D. & Uhlenbeck, O. C. (2004). Hasty decisions on the ribosome. *Nat Struct Mol Biol* 11, 206-8.

Studer, S. M., Feinberg, J. S. & Joseph, S. Rapid kinetic analysis of EF-G-dependent mRNA translocation in the ribosome. J Mol Biol 327, 369-81 (2003).

Uemura, S., C. E. Aitken, et al. (2010). "Real-time tRNA transit on single translating ribosomes at codon resolution." *Nature* 464(7291): 1012-7.

Villa, E., Sengupta, J., Trabuco, L. G., LeBarron, J., Baxter, W. T., Shaikh, T. R., Grassucci, R. A., Nissen, P., Ehrenberg, M., Schulten, K. & Frank, J. (2009). Ribosome-induced changes in elongation factor Tu conformation control GTP hydrolysis. *Proc Natl Acad Sci USA* 106, 1063-8.

Walker, S. E., Shoji, S., Pan, D., Cooperman, B. S. & Fredrick, K. Role of hybrid tRNA-binding states in ribosomal translocation. *Proc Natl Acad Sci USA* 105, 9192-7 (2008).

Wang, Y. et al. Single-molecule structural dynamics of EF-G-ribosome interaction during translocation. Biochemistry 46, 10767-75 (2007).

Yin, J., Lin, A. J., Golan, D. E. & Walsh, C. T. Site-specific protein labeling by Sfp phosphopantetheinyl transferase. Nat Protoc 1, 280-5 (2006).

Young, T. S. and C. T. Walsh (2011). "Identification of the thiazolyl peptide GE37468 gene cluster from *Streptomyces* ATCC 55365 and heterologous expression in *Streptomyces lividans.*" *PNAS* 108(32): 13053-13058.

Yusupov, M. M., Yusupova, G. Z., Baucom, A., Lieberman, K., Earnest, T. N., Cate, J. H. & Noller, H. F. (2001). Crystal structure of the ribosome at 5.5 A resolution. *Science* 292, 883-96.

Zhou, Z. et al. Genetically encoded short peptide tags for orthogonal protein labeling by Sfp and AcpS phosphopantetheinyl transferases. ACS Chem Biol 2, 337-46 (2007).

Zhou, Z., Koglin A., Wang, Y., McMahon, A. P. & Walsh, C. T. (2008). An eight residue fragment of an acyl carrier protein suffices for post-translational introduction of fluorescent pantetheinyl arms in protein modification in vitro and in vivo. J. Am. Chem. Soc. 130, 9925-9930.

Zhao, Y. Z., Terry, D., Shi, L., Weinstein, H., Blanchard, S. C. & Javitch, J. A. Single-molecule dynamics of gating in a neurotransmitter transporter homologue. Nature 465, 188-93 (2010).

---

We claim:

1. A composition comprising an elongation factor-Ts (EF-Ts) and a stable ternary complex of an elongation factor-Tu (EF-Tu), GTP and an aminoacylated tRNA (aa-tRNA), wherein the EF-Ts is in a binary complex with the EF-Tu and wherein at least 80% of the EF-Tu is labeled with a fluorophore or a fluorescence quencher, and wherein the aa-tRNA is labeled with a fluorophore when the EF-Tu is labeled with a quencher or the aa-tRNA is labeled with a quencher when the EF-Tu is labeled with a fluorophore, wherein the quencher is in sufficient proximity to the fluorophore to form a quenched ternary complex.

2. The composition of claim 1 wherein substantially all of said EF-Tu is labeled.

3. The composition of claim 1, wherein EF-Tu comprises a C-terminal tag for attachment of said fluorophore or said quencher.

4. The composition of claim 1, wherein said tag is an SFP tag as defined by SEQ ID NO: 2 or an acyl carrier protein (AcpS) tag.

5. The composition of claim 1, wherein a quencher is attached to an SFP tag as defined by SEQ ID NO: 2.

6. The composition of claim 1, wherein the label on the EF-Tu and the label the aa-tRNA does not perturb the nature or kinetics of ternary complex formation.

7. The composition of claim 6, wherein said quencher is Cy5Q and said donor fluorophore is Cy3.

8. A method for generating stable ternary-complexes which comprises
   (a) providing an EF-Tu, an EF-Ts, GTP and aa-tRNA;
   (b) allowing a stable ternary complex to form between said EF-Tu, said GTP and said aa-tRNA, where said EF-Tu is in a binary complex with said EF-Ts;
   (c) isolating said ternary complex with said EF-Tu in the binary complex with EFTs.

9. The method of claim 8 wherein said EF-Tu has a tag for addition of a quencher and said method further comprises reacting said ternary complex with a quencher for attachment to said EF-Tu.

10. An in vitro translation mixture comprising a quencher-labeled EF-Tu in a binary complex with EF-Ts and a fluorophore-labeled tRNA in a ternary complex with GTP.

11. A composition comprising a binary complex of a purified EF-Tu having native activity and a purified EF-Ts.

12. The composition of claim 11, wherein the EF-Tu is labeled with a fluorophore or a quencher.

13. The composition of claim 11 or 12 which further comprises GTP and a labeled or unlabeled tRNA or aa-tRNA.

14. The composition of claim 13, wherein said label is a fluorophore when EF-Tu is labeled with a quencher or said label is a quencher when EF-Tu is labeled with a fluorophore.

* * * * *

SEQUENCE LISTING

```
<160> NUMBER OF SEQ ID NOS: 2

<210> SEQ ID NO 1
<211> LENGTH: 431
<212> TYPE: PRT
<213> ORGANISM: E coli

<400> SEQUENCE: 1

Met Ser Tyr Tyr His His His His His Asp Tyr Asp Ile Pro Thr
1               5                   10                  15

Thr Glu Asn Leu Tyr Phe Gln Gly Ala Met Gly Ser Lys Glu Lys Phe
                20                  25                  30

Glu Arg Thr Lys Pro His Val Asn Val Gly Thr Ile Gly His Val Asp
            35                  40                  45

His Gly Lys Thr Thr Leu Thr Ala Ala Ile Thr Thr Val Leu Ala Lys
        50                  55                  60

Thr Tyr Gly Gly Ala Ala Arg Ala Phe Asp Gln Ile Asp Asn Ala Pro
65                  70                  75                  80

Glu Glu Lys Ala Arg Gly Ile Thr Ile Asn Thr Ser His Val Glu Tyr
                85                  90                  95
```

```
Asp Thr Pro Thr Arg His Tyr Ala His Val Asp Cys Pro Gly His Ala
            100                 105                 110

Asp Tyr Val Lys Asn Met Ile Thr Gly Ala Ala Gln Met Asp Gly Ala
        115                 120                 125

Ile Leu Val Val Ala Ala Thr Asp Gly Pro Met Pro Gln Thr Arg Glu
130                 135                 140

His Ile Leu Leu Gly Arg Gln Val Gly Val Pro Tyr Ile Ile Val Phe
145                 150                 155                 160

Leu Asn Lys Cys Asp Met Val Asp Asp Glu Glu Leu Leu Glu Leu Val
                165                 170                 175

Glu Met Glu Val Arg Glu Leu Leu Ser Gln Tyr Asp Phe Pro Gly Asp
            180                 185                 190

Asp Thr Pro Ile Val Arg Gly Ser Ala Leu Lys Ala Leu Glu Gly Asp
        195                 200                 205

Ala Glu Trp Glu Ala Lys Ile Leu Glu Leu Ala Gly Phe Leu Asp Ser
    210                 215                 220

Tyr Ile Pro Glu Pro Glu Arg Ala Ile Asp Lys Pro Phe Leu Leu Pro
225                 230                 235                 240

Ile Glu Asp Val Phe Ser Ile Ser Gly Arg Gly Thr Val Val Thr Gly
                245                 250                 255

Arg Val Glu Arg Gly Ile Ile Lys Val Gly Glu Glu Val Glu Ile Val
            260                 265                 270

Gly Ile Lys Glu Thr Gln Lys Ser Thr Cys Thr Gly Val Glu Met Phe
        275                 280                 285

Arg Lys Leu Leu Asp Glu Gly Arg Ala Gly Glu Asn Val Gly Val Leu
    290                 295                 300

Leu Arg Gly Ile Lys Arg Glu Glu Ile Glu Arg Gly Gln Val Leu Ala
305                 310                 315                 320

Lys Pro Gly Thr Ile Lys Pro His Thr Lys Phe Glu Ser Glu Val Tyr
                325                 330                 335

Ile Leu Ser Lys Asp Glu Gly Gly Arg His Thr Pro Phe Phe Lys Gly
            340                 345                 350

Tyr Arg Pro Gln Phe Tyr Phe Arg Thr Thr Asp Val Thr Gly Thr Ile
        355                 360                 365

Glu Leu Pro Glu Gly Val Glu Met Val Met Pro Gly Asp Asn Ile Met
    370                 375                 380

Val Val Thr Leu Ile His Pro Ile Ala Met Asp Asp Gly Leu Arg Phe
385                 390                 395                 400

Ala Ile Arg Glu Gly Gly Arg Thr Val Gly Ala Gly Val Val Ala Lys
                405                 410                 415

Val Leu Ser Gly Asp Ser Leu Ser Trp Leu Leu Arg Leu Leu Asn
            420                 425                 430

<210> SEQ ID NO 2
<211> LENGTH: 12
<212> TYPE: PRT
<213> ORGANISM: Artificial Sequence
<220> FEATURE:
<223> OTHER INFORMATION: SFP tag

<400> SEQUENCE: 2

Gly Asp Ser Leu Ser Trp Leu Leu Arg Leu Leu Asn
1               5                   10
```